(12) United States Patent
Elmaleh et al.

(10) Patent No.: US 7,632,485 B2
(45) Date of Patent: Dec. 15, 2009

(54) CATALYTIC RADIOFLUORINATION

(75) Inventors: David R. Elmaleh, Newton, MA (US); Alan J. Fischman, Boston, MA (US); Timothy M. Shoup, Decatur, GA (US)

(73) Assignee: Massachusetts General Hospital, Charlestown, MA (US)

( * ) Notice: Subject to any disclaimer, the term of this patent is extended or adjusted under 35 U.S.C. 154(b) by 107 days.

(21) Appl. No.: 11/065,345

(22) Filed: Feb. 24, 2005

(65) Prior Publication Data

US 2005/0260130 A1 Nov. 24, 2005

Related U.S. Application Data

(60) Provisional application No. 60/547,206, filed on Feb. 24, 2004.

(51) Int. Cl.
*A61K 51/00* (2006.01)
*A61M 36/14* (2006.01)
*C07F 5/00* (2006.01)

(52) U.S. Cl. .................... 424/1.89; 424/1.65; 424/1.85; 534/11

(58) Field of Classification Search ................ 424/1.85, 424/1.89; 534/11
See application file for complete search history.

(56) References Cited

U.S. PATENT DOCUMENTS

| | | | | |
|---|---|---|---|---|
| 4,433,164 | A | * | 2/1984 | Jenck .......................... 560/207 |
| 4,446,123 | A | * | 5/1984 | Woo .......................... 424/1.65 |
| 6,224,849 | B1 | | 5/2001 | Kennis et al. |
| 2002/0098148 | A1 | | 7/2002 | Miller et al. |

FOREIGN PATENT DOCUMENTS

| | | |
|---|---|---|
| EP | 1563852 A | 8/2005 |
| WO | WO 03/065882 A | 8/2003 |
| WO | WO-2003/065882 | 8/2003 |
| WO | WO-2005/081425 | 9/2005 |

OTHER PUBLICATIONS

International Search Report dated Jun. 3, 2005.
Kuhnast, B. et al., "Fluorine-18 labeling of peptide nucleic acids", *J. Label. Compd. Radiopharm.*, 45(1):1-11 (John Wiley & Sons, Ltd,. Chichester, Great Britain, 2002).
Patt, J. T. et al., "Reactions of [$^{18}$F]4-fluorobenzenediazonium cations with cysteine or the cysteinyl group: preparation of $^{18}$F-labeled S-aryl-cysteine and a radiolabeled peptide", *J. Label. Compd. Radiopharm.*, 45(14):1229-1238 (John Wiley & Sons, Ltd., Chichester, Great Britain, Jan. 1, 2002).
Vandecapelle, M. et al., "Synthesis and preliminary in vivo evaluation of 4-[$^{18}$F]fluoro-N-{2-[4-(6-trifluoromethylpyridin-2-yl)piperazin-1-yl]ethyl}benzamide, a potential PET radioligand for the 5-HT$_{1A}$ receptor", *J. Label. Compd. Radiopharm.*, 47(9):531-542 (John Wiley & Sons, Ltd., Chichester, Great Britain, Aug. 2004).
International Search Report dated Jun. 2, 2008.
Tewson, T. J. et al. "Preparation of Fluorine-18 Aryl Fluorides: Piperidyl Triazenes as a Source of Diazonium Salts," *J.C.S. Chem. Comm.* 1979, 1149-1150.
Berridge, M. S. et al. "Design and Synthesis of $^{18}$F-Labeled Neurotoxic Analogs of MPTP," *J. Med. Chem.* 1993, 36, 1284-1290.
Cai. L. et al. "Chemistry with [$^{18}$F]Fluoride Ion," *Eur. J. Org. Chem.* 2008, 2853-2873.

* cited by examiner

*Primary Examiner*—Michael G Hartley
*Assistant Examiner*—Melissa Perreira
(74) *Attorney, Agent, or Firm*—Beth E. Arnold, Esq.; Foley Hoag LLP

(57) ABSTRACT

One aspect of the present invention relates to a method of preparing radiofluorinated substituted alkyl, cycloalkyl, aryl, and alkenyl compounds. In a preferred embodiment, potassium fluoride-18 is used. Another aspect of the invention relates to piperazine compounds containing fluorine-18 that are useful as imaging agents. In certain embodiments, the piperazine compounds contain a quaternary amine. Another aspect of the invention relates to arylphosphonium compounds containing fluorine-18 that are useful as imaging agents. In certain embodiments, the phosphonium compound is a tetraaryl phosphonium salt. Another aspect of the present invention relates to a method of obtaining a positron emission image of a mammal, comprising the steps of administering to a mammal a compound of the invention, and acquiring a positron emission spectrum of the mammal.

6 Claims, 12 Drawing Sheets

Mechanism:

CATALYTIC RADIOFLUORINATION

RELATED APPLICATIONS

This application claims the benefit of priority to U.S. Provisional Patent Application Ser. No. 60/547,206, filed Feb. 24, 2004; the contents of which are incorporated by reference.

BACKGROUND OF THE INVENTION

Contemporary medical imaging depends largely upon the use of radioisotopes. One of the first clinically-employed radioisotopes was technetium (Tc). This element was first administered to a human subject in 1961 in the form of Na$^{99m}$TcO$_4$. Other radioisotopes, including halogens, such as $^{125}$I, $^{131}$I and $^{82}$Br, and isotopes of various metal radionuclides of lead, gallium, rhenium, arsenic and copper, have also been explored as potential imaging agents. Medical imaging is used in a variety of medical applications, including imaging of the brain, tumors, and components of the cardiovascular system.

Blood flow imaging agents are currently the most important tool for determining heart function. Tl-201, Tc-99-MIBI and Tc-99-tetrofosmin are in routine use for myocardial imaging at rest and after exercise. These agents are very useful but are not optimal. These tracers are Single Photon Imaging agents and their resolution is limited to the properties of SPECT imaging cameras and technology. However, fluorine-18 can be detected by Positron Emission Tomography imaging technology which has several advantages including higher resolution and corrections for the emitted radiation attenuation. In fact, the number of PET cameras and imaging centers are growing rapidly in respone to the superior performance properties of fluorine-18.

F-18 is one of the most useful positron emitting radionuclides currently being used in clinical nuclear medicine diagnosis. For example, 2-[F-18] FDG (2-[F-18]-fluoro-2-dexoy-D-glucose) is the radiopharmaceutical of choice for the diagnosis of several cancers and brain disorders. This radiopharmaceutical agent produces superior high-resolution images and quantitative regional uptake of tissues. The 110-min half-life of fluorine-18 allows production and distribution of 2-[F-18] FDG to nuclear medicine facilities near a cyclotron center. The relatively long physical half-life of fluorine-18 also permits PET studies of moderately slow physiological process. Decay of fluorine-18 is largely by positron emission (97%), and the emitted positron is of relatively low energy (maximum 0.635 MeV) and thus has a short mean range (2.39 mn in water). Fluorine-18 is readily available from both particle accelerators and nuclear reactors using a wide variety of nuclear reactions, and can be produced at specific activities approaching the theoretical limit of $1.171 \times 10^9$ Ci/mmol.

In addition to their superior medical imaging properties, fluorine atoms are a component of many pharmaceutical compounds. Fluorine can function as a substitute for a hydrogen atom in many biologically active molecules without substantially altering their properties, as done in the case of 2-deoxy-D-glucose.

Despite the utility of F-18, there are only a very small number of methods to introduce F-18 into organic molecules. To date, the introduction of F-18 to a single bond was made via an exchange reaction on mesylate or triflate. Alternatively, F-18 could be introduced onto a C—C double bond or aromatic ring via an appropriate tin compound and [F-18]F$_2$ or using anhydrous [F-18]fluoride on an electron withdrawing activated ring. The exchange reaction is carried out by treating the mesylate or triflate with a mixture of F-18, potassium carbonate, and crown ether, such as Kryptofix. 2-[F-18] FDG is the best example of that reaction. Other reactions using, [F-18]-F$_2$, [F-18]XeF$_2$, [F-18]DAST, [F-18]triethylammonium fluoride were also reported for specific radiolabeling. Radiofluorination of tributyltin-substituted double bonds and aromatic rings used [F-18]F$_2$ as a reagent. However, the specific activity of these radiofluorinations is very low due to the cold F$_2$ carrier. Radiofluorination of a nitro moiety on an activated aromatic ring with F-18 anhydrous fluoride was also reported. However, most fluorine-containing drugs are not activated with electron withdrawing groups, such as nitro, aldehyde, ketone, ester or others; therefore, this reaction is not applicable for a large number of compounds.

There is an urgent need for the development of new agents that can improve the diagnosis of heart disease by understanding the molecular behavior, physiology, anatomy, and function of the myocardium. However, many biologically-active molecules, drugs, receptor ligands, peptides, and proteins are not readily available for clinical nuclear medicine due to the limitations inherent in the methods used to install F-18. Therefore, the need exists for a new method for labeling a compound with F-18 which is amenable to a wide variety of organic substrates.

SUMMARY OF THE INVENTION

One aspect of the present invention relates to a method of preparing fluorosubstituted alkyl, cycloalkyl, aryl, and alkenyl compounds. In certain embodiments, anhydrous potassium flouride is reacted with an alkyl or cycloalkyl sulfonate, e.g., a mesylate. In certain embodiments, anhydrous potassium flouride is reacted with a nitroaromatic compound. In a preferred embodiment, the reaction is conducted in the presence of Kryptofix. In a preferred embodiment, potassium fluoride-18 is used.

Another aspect of the invention relates to piperazine compounds containing fluorine-18 that are useful as imaging agents. In certain embodiments, the piperazine compounds contain a quaternary amine. In certain embodiments, the piperazine compounds are N-substituted by a cycloalkyl or aryl group. In a preferred embodiment, the piperazine compounds are substituted at the 4-position with a phenyl group and substituted at the 1-position by a fluorocycloalkyl group.

Another aspect of the invention relates to arylphosphonium compounds containing fluorine-18 that are useful as imaging agents. In certain embodiments, the phosphonium compound is a tetraarylphosphonium salt. In a preferred embodiment, the arylphosphonium compound is a tetraphenylphosphonium salt.

Another aspect of the present invention relates to a method of obtaining a positron emission image of a mammal, comprising the steps of administering to a mammal a compound of the invention, and acquiring a positron emission spectrum of the mammal. In a preferred embodiment, the compound of the invention is a piperazine substituted with fluorine-18.

DETAILED DESCRIPTION OF THE INVENTION

Radioisotope Imaging

Figure 1:
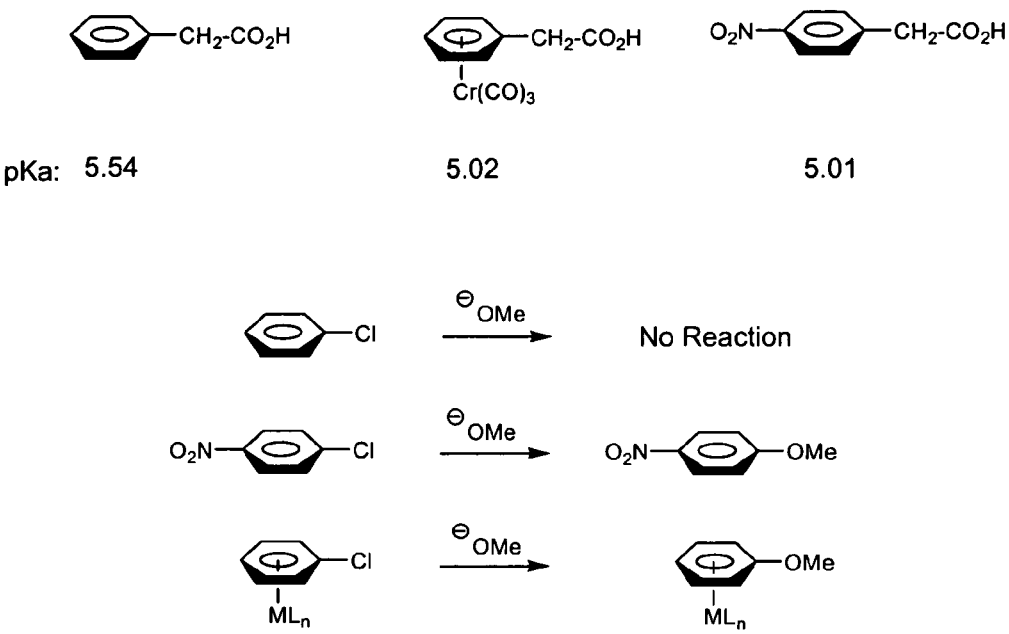
FIG. 1 depicts various metal-activated arenes.
Figure 1:
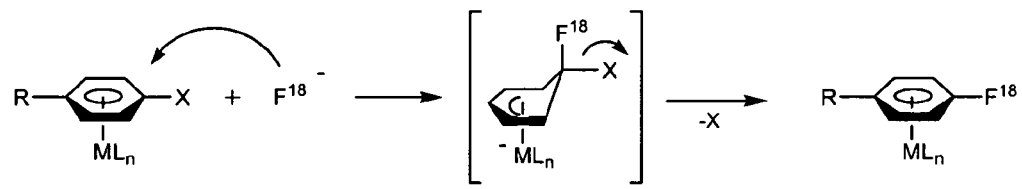

Thallium-201, Tc-99-sestamibi and tetrofosmin are currently the most widely used radiopharmaceutical for clinical evaluation of myocardial perfusion. However, the widespread use of PET (Position Emission Tomography) technology and the limitations of these agents with respect to their properties as SPECT agents has stimulated the search for more suitable PET tracers. Most approaches for developing a myocardial perfusion agent have generally involved the incorporation of iodine-123 or technetium-99m into a cationic moiety, thereby taking advantage of the better radionuclidic properties of iodine and technetium while potentially retaining the distributional properties of monocationic thallium(I) species. Numerous publications have described the above single-photon-emission computed tomographic (SPECT) commercial agents for research and clinical diagnosis of heart disease. An alternative method for designing a blood flow agent is the use of a freely diffusible agent like antipyrine. However, this approach is often avoided due the difficulties in modeling and the required fast kinetic data collection for these agents as compared to agents that are freely diffusible and significantly trapped in the tissue.

The widespread use of F-18 FDG and the exponential increase in PET scanners focused our effort on developing an appropriate F-18 lipophilic cationic agent. We developed two series of agents based on the modification of charged piperazinium salts and of tetraphenylphosphonium salts. The synthesis and F-18 radiolabeling of these salts is not trivial due to the need for a suitable precursor and the appropriate conditions for radiolabeling. Here we describe several specific structures and their analogs as blood flow agents. We have devised syntheses and radiolabeling procedures for these agents.

Catalytic Radiohalogenation

The catalytic radiohalogenation reaction of the invention involves reacting anhydrous potassium halide, a crown ether, and an organic compound that has a leaving group. In a preferred embodiment, the radiohalogenation is a radiofluorination. The reaction proceeds by substitution of the leaving group by the halide. Importantly, the reaction of the present invention does not require that the compound contain an activating group to enhance the reactivity of the leaving group. For example, the radiofluorination reaction of the invention works on unactivated nitroaryl groups, e.g., nitrophenyl groups. The fact that the radiofluorination reaction of the invention works on both "activated" and "unactivated" compounds is an important breakthrough and will allow for the facile preparation of many $^{18}$F-labeled compounds useful for medical imaging.

In addition, the reaction can be conducted in the presence or absence of solvent. For reactions conducted in the presence of the solvent, the reaction should be amenable to most organic solvents which do not have a hydroxyl group which might react with the substrates of the reaction. A representative selection of suitable solvents includes acetonitrile, dimethylacetamide, dimethylformamide, dimethylsulfoxide, dioxane, benzene, toluene, xylene, ethylbenzene diglyme, dimethoxyethane (glyme), diethylene glycol dibutyl ether, triethylene glycol dimethyl ether, tetraethylene glycol dimethyl ether, polyethylene glycol dimethyl ethers, diethylene glycol dibutyl ether, polyethylene glycol dibutyl ethers, heptane, octane, butylacetate and the like. The ideal solvent for a particular reaction can be determined by one of ordinary skill in the art taking into consideration the preferred temperature of the reaction, the boiling point of the solvent, and the solubilities of the substrates in the solvent.

In certain embodiments, the crown either is Kryptofix. A variety of Kryptofix compositions will work in the instant invention including: 1,4,10-Trioxa-7,13-diaza-cyclopentadecane (Kryptofix® 21), 4,7,13,16,21,24-Hexaoxa-1,10-diazabicyclo[8.8.8]hexacosane (Kryptofix® 222), 4,7,13,16,21-Pentaoxa-1,10-diazabicyclo[8.8.5]tricosane (Kryptofix® 221), and 4,7,13,18-Tetraoxa-1,10-diazabicyclo[8.5.5] eicosane (Kryptofix® 211).

The optimal reaction temperature can be adjusted to take into consideration the reactivity of the leaving group and the boiling point of the solvent used in the reaction. In the absence of solvent, the reaction can be conducted at temperatures up to about 200° C. The relatively high reaction temperature minimizes the reaction time. Alternatively, a reaction temperature of about 120° C. is optimal for certain substrates when acetonitrile is used as the solvent. The fluorination reaction can be carried out at lower reaction temperatures. Lower reaction temperatures can be beneficial for substrates that may decompose at elevated temperatures. However, the reaction must be conducted over a longer time period to reach completion when the reaction is performed at a lower temperature. In certain embodiments, the reaction is conducted a temperature of at least about 25° C., 40° C., 50° C., or 75° C. In a more preferred embodiment, the reaction the reaction is conducted a temperature of at least about 100° C., 110° C, 120° C.,or 140° C. In certain embodiments, the reaction is conducted at a temperature of at least about 180° C., 200° C., or 220° C. Generally, reactions conducted near about 200° C. are performed without solvent.

The leaving group can be any chemical fragment that is capable of being displaced by the halogen nucleophile. In certain embodiments, the leaving group is an acetate, sulfonate, phosphate, halogen, nitro group, and the like. In a preferred embodiment, the leaving group is a mesylate, trifluoromethanesulfonate, or nitro group. The leaving group may be attached to a primary or second carbon atom of an alkyl or cycloalkyl group. In addition, the halogenation reaction of the invention also works for leaving groups that are attached to an aromatic ring. In a preferred embodiment, the aromatic ring is a benzene ring and the leaving group is a nitro group.

The halogenation reaction of the invention works best when the reaction conditions are anhydrous. In certain embodiments, the reaction is conducted in the presence of less than about 5%, 3%, 2%, 1%, 0.5%, or 0.1% water. In a preferred embodiment, the reaction conditions are anhydrous. It is important that any water is substantially removed from solvents that are used. In addition, it is important that the potassium fluoride is anhydrous. In certain embodiments, the potassium fluoride contains less than about 3%, 2%, 1%, 0.5%, or 0.1% water by weight. In a preferred embodiment, the potassium fluoride contains less than about 1% water by weight.

The halogenation reaction of the invention can be performed using halogen sources other than potassium fluoride. For example, the potassium cation can be substituted by a lithium, sodium, cesium, or rubidium cation. In addition, the potassium cation can be substituted by a positively charged transition metal, including a lanthanide or actinide. In certain embodiments, the potassium cation can be replaced by a tetralkylammonium cation, e.g., tetrabutyl ammonium. The halogenation reaction of the invention can be used to introduce isotopes of fluoride, such as $^{18}F$. In certain embodiments, the halogenation reaction of the invention can be used to introduce isotopes of iodide, bromine or chlorine. In a certain instances, the iodide is a radioisotope, e.g., $^{123}I$, $^{124}I$, $^{125}I$ or $^{131}I$. In certain instances, the chloride is a radioisotope, e.g., $^{36}Cl$. In certain instances, the bromine is a radioisotope, e.g., $^{77}Br$, $^{80}Br$ or $^{82}Br$.

In certain embodiments, the reaction may proceed more quickly in the presence of a transition metal. Certain transition metals are known to complex to aromatic carbon atoms, thereby rendering the carbon atoms more susceptible to attack by a nucleophile. Certain transition metals have energetically accessible d-orbitals, which are only partially filled with electrons. The number and shape of these orbitals contribute to the large number of reaction pathways that are made possible by these catalysts. Metal-activated arenes undergo nucleophilic reactions (FIG. 1). The metal acts as a strong electron-withdrawing group often compared to a nitro group, thus arenes can accept electron density from incoming nucleophiles.

The radiofluorination reaction is amenable to a wide variety of compounds including sulfonate, nitro, acetate or halogen derivates of alkyl, cycloalkyl, aryl, heteroaryl, aralkyl or alkenyl compounds. In certain preferred embodiments, the radiofluorination substrate is a nitroaromatic compound, alkyl mesylate, or cycloalkylmesylate. Alkenyl halides and alkenyl acetates would also be amenable to the reaction conditions. The following prophetic examples illustrate that the radiofluorination reaction of the invention could be used to prepare F-18 labeled alkenyl compounds.

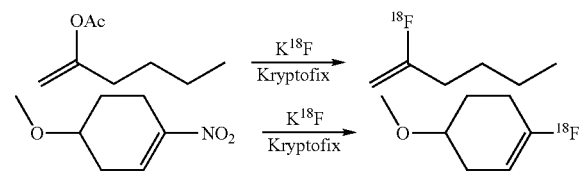

Another aspect of the present invention relates to a method of preparing aryl halides by reacting a triazine with sodium iodide and chlorotrimethylsilane. In a preferred embodiment, the iodide is radioactive. In certain embodiments, the iodide is $^{123}I$, $^{124}I$, $^{125}I$ or $^{131}I$. In a preferred embodiment, the iodide is $^{125}I$. The reaction can be conducted in the presence or absence of solvent. For reactions conducted in the presence of the solvent, the reaction should be amenable to most organic solvents which do not have a hydroxyl group that might react with the substrates of the reaction. A representative selection of suitable solvents includes acetonitrile, dimethylacetamide, dimethylformamide, dimethylsulfoxide, dioxane, benzene, toluene, xylene, ethylbenzene diglyme, dimethoxyethane (glyme), diethylene glycol dibutyl ether, triethylene glycol dimethyl ether, tetraethylene glycol dimethyl ether, polyethylene glycol dimethyl ethers, diethylene glycol dibutyl ether, polyethylene glycol dibutyl ethers, heptane, octane, butylacetate and the like. The ideal solvent for a particular reaction can be determined by one of ordinary skill in the art taking into consideration the preferred temperature of the reaction, the boiling point of the solvent, and the solubilities of the substrates in the solvent.

The optimal reaction temperature can be adjusted to take into consideration the thermal sensitivity of the substrate and the boiling point of the solvent used in the reaction. For example, a reaction temperature of about 120° C. is optimal for certain substrates when acetonitrile is used as the solvent. The iodination reaction can be carried out at lower reaction temperatures. Lower reaction temperatures can be beneficial for substrates that may decompose at elevated temperatures. However, the reaction will generally require more time to reach completion when the reaction is performed at a lower temperature. In certain embodiments, the reaction is conducted a temperature of at least about 25° C., 40° C., 50° C., or 75° C. In a more preferred embodiment, the reaction is conducted a temperature of at least about 100° C., 110° C., 120° C., or 140° C. However in certain embodiments, the reaction may be conducted at a temperature of at least about 150° C. or 180° C.

The halogenation reaction of the invention can be performed using halogen sources other than sodium iodide. For example, the sodium cation can be replaced by a lithium, potassium, cesium, or rubidium cation. In addition, the sodium cation can be replaced by a positively charged transition metal, including a lanthanide or actinide. The halogenation reaction of the invention can also be used to introduce isotopes of iodide, such as $^{123}I$, $^{124}I$, $^{125}I$ or $^{131}I$. In certain embodiments, the halogenation reaction of the invention can be used to introduce fluoride, chloride or bromide. In a certain embodiments, the fluoride is a radioisotope, e.g., $^{18}F$. In certain instances, the chloride is a radioisotope, e.g., $^{36}Cl$. In certain instances, the bromine is a radioisotope, e.g., $^{77}Br$, $^{80}Br$ or $^{82}Br$.

The chlorosilane can be any trialkylchlorosilane, triarylchlorosilane, triaralkylchlorolsilane, or a chlorosilane that has 1-2 alkyl groups and 1-2 aryl groups, such that the sum of the number of alkyl and aryl groups is equal to three. In certain embodiments, the chlorosilane is tert-butyl dimethylchlorosilane, triethylchlorosilane, triethylchlorosilane, or trimethylchlorosilane, diphenylchloromethylsilane. In a preferred embodiment, the chlorosilane is trimethylchlorosilane.

The present invention provides a method for the introduction of fluoride-18 to many organic molecules using a catalytic exchange reaction. One advantage of this method is its simplicity and its potential to allow the radiolabeling of many biologically active molecules with a simple form of fluoride-18 produced on a routine basis in many facilities. This method will allow widespread production and use of many new and valuable radiopharmaceuticals. The radiofluorination method of the invention is useful for installation of fluoride- 18 and other halogens on single, double or aromatic bonds, i.e., sp$^3$-hybridized and sp$^2$-hybridized carbons.

Biodistribution Analysis

Rats

CD Fischer rats (175-200 g) will be anesthetized with ether, and 0.2 mL (20-40 mCi) of the F-18-labeled compound will be injected via the tail vein. Groups of six rats each will be sacrificed by ether asphyxiation at 5, 30 and 60 min post administration. The appropriate organs will be excised, blotted dry, weighed, and assayed for radioactivity in a NaI(T1) gamma well scintillation counter. Blood will be obtained from a vein in the thoracic cavity and assayed for radioactivity.

Monkeys

The animals will be positioned in the micro PET tomographic camera, and 2 to 5 mCi of the F-18-methylated phenylpiperazinium derivative in 2.5 mL of 0.9% saline will be injected iv over several seconds. PET data will be collected over a 1-h period and 10-sec integration exposures will be used for the first 10 min and 1-min exposures thereafter. The data will be corrected for scatter, accidental coincidences, self-absorption and detector uniformity variations. Quantitative tomographic constructions will be then computed. Time-activity curves for regions of interest will be collected.

The parameters of interest in the evaluation of these radiochemicals as potential myocardial imaging agents include uptake in the heart, selectivity for the heart compared to surrounding tissues such as the liver, lungs, and blood, as well as retention of activity in the heart.

According to the present invention, [F-18]-1-methyl-1-(fluoroalkyl)-4-phenylpiperazinium derivatives can be readily prepared and they possess marked myocardial uptake and selectivity. The radiolabeled compounds will localize rapidly in the rat myocardium to give both high uptake, good target to non-target selectivity with significant retention. The tissue distribution will be compared to that of the $^{125}$I-labeled compounds which were previously evaluated. Further preclinical studies will compare the distribution of these agents to microspheres and other perfusion markers.

Method for Validating an Agent as a Blood-Flow Agent by PET Imaging and Microsphere Injection Animals (pigs or rats) are prepared according to an accepted protocol, in brief, by inserting a catheter in the carotid artery and the femoral vein. The animals are positioned in the PET camera.

Two sets with different tag microspheres and blood flow agent are injected in a two-part experiment as follows. In both parts, microspheres are injected in one line (arterial) and blood collected from the other using pumps with specific flow rates. 1. The first injection is at the normal blood flow state of the animal. A [F-18] blood flow agent and the first tag microspheres are injected. Blood sampling with a known flow rate are drawn and an imaging schedule with PET is performed (see below image collection schedule) and 2. The second tag microspheres and the same [F-18] blood flow agent are injected after increasing the blood flow by an adenosine bolus injection. The blood drawing and imaging schedule is repeated as above. At the end of the second imaging procedure the animal is sacrificed, the heart is removed and the blood and heart tissue are counted for microspheres concentrations. Blood flow is calculated counted. (Carter, E., *J. Appl. Physiol.*, 1988). The increase in blood flow measured by the microspheres (gold standard) is compared to the one obtained by imaging. In the human microsphere imaging measurements are not allowed.

Methods for Monitoring Blood Flow and Membrane Transport

Imaging Schedule: For purposes of PET imaging, the animals are positioned in the positron camera using a plastic-imaging cradle. Prior to imaging, transmission data will be acquired with rotating pin source containing 68Ga for subsequent attenuation correction of PET scans. After injection with approximately 2-10 mCi of the [18F]blood flow agent, arterial blood samples will be obtained at 1, 3, 6, 9, 12, 15, 20, 25, 30, and 60 min. Sequential imaging collections of 30-60 second frames are obtained and the pharmacokinetics of the blood flow agent in the heart is determined by plotting heart activity as a function of time.

The procedure for monitoring membrane transport is analagous to that described for monitoring blood flow.

Definitions

For convenience, certain terms employed in the specification, examples, and appended claims are collected here.

The term "leaving group" refers to a functionality which upon bond cleavage departs with an electron pair. In general, good leaving groups are those moieties which are expelled from the substrate as weak bases. For example, sulfates, sulfonates, chloride, bromide, iodide, phosphates and the like are good leaving groups. In addition, some moieties may be good leaving groups when protonated or complexed with a Lewis acid. For example, alkoxide ions are generally poor leaving groups, but alcohols are good leaving groups. It should be noted that ring strain may, in some cases, allow a rather poor leaving group to be expelled, as in the case of epoxides, aziridines, and the like.

The term "crown ether" refers to a cyclic molecule in which ether groups (i.e., polyethers) are connected by dimethylene linkages.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

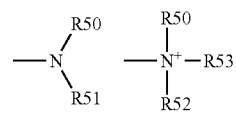

wherein R50, R51 and R52 each independently represent a hydrogen, an alkyl, an alkenyl, —(CH$_2$)$_m$-R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

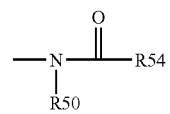

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

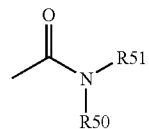

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

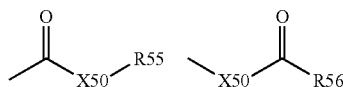

wherein X50 is a bond or represents an oxygen or a sulfur, and R55 and R56 represents a hydrogen, an alkyl, an alkenyl, $-(CH_2)_m$-R61 or a pharmaceutically acceptable salt, R56 represents a hydrogen, an alkyl, an alkenyl or $-(CH_2)_m$-R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to $-O(C=O)NRR'$, where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

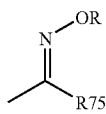

wherein R75 is hydrogen, alkyl, cycloalkyl, alkenyl, alkynyl, aryl, aralkyl, or $-(CH_2)_m$—R61. The moiety is an "oxime" when R is H; and it is an "oxime ether" when R is alkyl, cycloalkyl, alkenyl, alkynyl, aryl, aralkyl, or $-(CH_2)_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of $-O$-alkyl, $-O$-alkenyl, $-O$-alkynyl, $-O-(CH_2)_m$-R61, where m and R61 are described above.

The term "sulfonate" is art recognized and refers to a moiety that may be represented by the general formula:

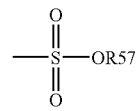

in which R57 is an electron pair, hydrogen, alkyl, cycloalkyl, or aryl.

The term "sulfate" is art recognized and includes a moiety that may be represented by the general formula:

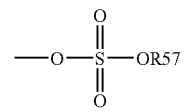

in which R57 is as defined above.

The term "sulfonamido" is art recognized and includes a moiety that may be represented by the general formula:

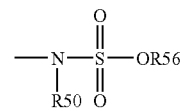

in which R50 and R56 are as defined above.

The term "sulfamoyl" is art-recognized and refers to a moiety that may be represented by the general formula:

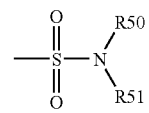

in which R50 and R51 are as defined above.

The term "sulfonyl" is art-recognized and refers to a moiety that may be represented by the general formula:

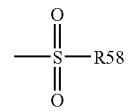

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

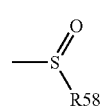

in which R58 is defined above.

The term "phosphoryl" is art-recognized and may in general be represented by the formula:

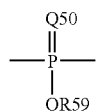

wherein Q50 represents S or O, and R59 represents hydrogen, a lower alkyl or an aryl. When used to substitute, e.g., an alkyl, the phosphoryl group of the phosphorylalkyl may be represented by the general formulas:

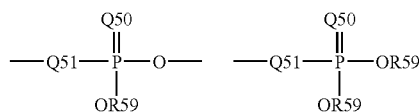

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

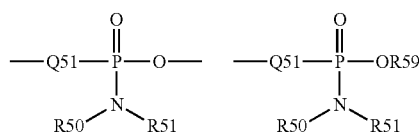

wherein Q51, R50, R51 and R59 are as defined above.

The term "phosphonamidite" is art-recognized and may be represented in the general formulas:

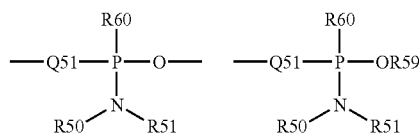

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2nd ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

Compounds of the Invention

One aspect of the current invention relates to F-18 cationic and cationic lipophilic compounds useful as blood flow markers for myocardial PET imaging. In certain embodiments, the compounds are charged phenylpiperazine and tetraphenylphosphonium compounds. The compounds of the invention have superior properties to other imaging agents because F-18 is a better radiolabel than Tc-99m (PET Vs. SPECT). For example, the high resolution and shorter half-life of F-18 render it a superior agent for imaging. In addition, the compounds of the invention should exhibit: 1) behavior similar to that of microspheres, as opposed to free diffusion in and out of the cell; and 2) receptor-binding advantages due to the piperazine core. Moreover, F-18 tetraphenyl phosphonium compounds are potentially useful for imaging brain tumors. The superior technical attributes of these compounds relate in part to the fact that such PET imaging agents are more suitable for regional quantitation of a measured physiological parameter due to the simultaneous coincidence detection (180°) of the positron inhalation. This in turn increases the accuracy and sensitivity to in-depth resolution. In addition, tetraphenylphosphonium agents can be used to image tumors, although not necessarily brain tumors. Tetraphenylphosphonium agents will concentrate in tumors that have enhanced negative charge on cell membrane and mitochondria, such as breast carcinoma. Finally, the compounds of the present invention may be used to assess qualitatively and quantitatively blood flow and membrane transport in a mammal.

One aspect of the present invention relates to a compound represented by formula I:

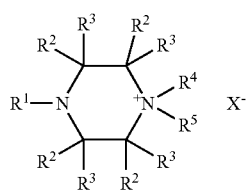

I wherein $R^1$ is H, alkyl, cycloalkyl, alkenyl, alkynyl, aryl, heteroaryl, aralkyl, heteroaralkyl, acyl, alkylsulfonyl, arylsulfonyl, aralkylsulfonyl, or $-CO_2R^6$;

$R^2$ represents independently for each occurrence H, alkyl, halogen, hydroxyl, amino, aminoalkyl, or alkoxyl;

$R^3$ represents independently for each occurrence H, alkyl, or halogen;

$R^4$ is alkyl or aralkyl;

$R^5$ is fluorosubstituted alkyl, fluorosubstituted cycloalkyl, fluorosubstituted aryl, fluorosubstituted aralkyl, or fluorosubstituted alkenyl; and said fluoro substituent comprises $^{18}F$;

X is an anion that has an overall charge of −1; and

R is H, alkyl, aryl, or aralkyl.

In certain embodiments, the present invention relates to compound I, wherein said compound has a radioactivity of greater than or equal to about 1 Curie/mmol.

In certain embodiments, the present invention relates to compound I, wherein said compound has a radioactivity of greater than or equal to about 5 Curie/mmol.

In certain embodiments, the present invention relates to compound I, wherein said compound has a radioactivity of greater than or equal to about 10 Curie/mmol.

In certain embodiments, the present invention relates to compound I, wherein said compound has a radioactivity of greater than or equal to about 100 Curie/mmol.

In certain embodiments, the present invention relates to compound I, wherein said compound has a radioactivity of greater than or equal to about 1,000 Curie/mmol.

In certain embodiments, the present invention relates to compound I, wherein $R^1$ is H, alkyl, cycloalkyl, or aryl.

In certain embodiments, the present invention relates to compound I, wherein $R^1$ is H.

In certain embodiments, the present invention relates to compound I, wherein $R^1$ is aryl.

In certain embodiments, the present invention relates to compound I, wherein $R^1$ is a phenyl group.

In certain embodiments, the present invention relates to compound I, wherein $R^2$ and $R^3$ represent independently for each occurrence H or alkyl.

In certain embodiments, the present invention relates to compound I, wherein $R^2$ and $R^3$ represent independently for each occurrence H.

In certain embodiments, the present invention relates to compound I, wherein $R^4$ is alkyl.

In certain embodiments, the present invention relates to compound I, wherein $R^4$ is methyl, ethyl, propyl, isopropyl, butyl, isobutyl, sec-butyl, or pentyl.

In certain embodiments, the present invention relates to compound I, wherein $R^4$ is methyl.

In certain embodiments, the present invention relates to compound I, wherein $R^5$ is fluorosubstituted alkyl, fluorosubstituted cycloalkyl, or fluorosubstituted aryl.

In certain embodiments, the present invention relates to compound I, wherein $R^5$ is fluorosubstituted cycloalkyl.

In certain embodiments, the present invention relates to compound I, wherein R5 is fluorosubstituted cyclopropyl, fluorosubstituted cyclobutyl, fluorosubstituted cyclopentyl, fluorosubstituted cyclohexyl, fluorosubstituted cycloheptyl, or fluorosubstituted cyclooctyl.

In certain embodiments, the present invention relates to compound I, wherein $R^5$ is fluorosubstituted cyclobutyl or fluorosubstituted cyclohexyl.

In certain embodiments, the present invention relates to compound I, wherein $R^5$ is 2-fluorocyclobutyl or 4-fluorocyclohexyl.

In certain embodiments, the present invention relates to compound I, wherein $R^5$ is fluorosubstituted aryl.

In certain embodiments, the present invention relates to compound I, wherein $R^5$ is fluorosubstituted phenyl.

In certain embodiments, the present invention relates to compound I, wherein $R^5$ is 4-fluorophenyl.

In certain embodiments, the present invention relates to compound I, wherein X is halide, acetate, nitrate, sulfonate, $PO_4M_2$, $SO_4M$, valerate, oleate, palmitate, stearate, laurate, or benzoate; wherein M is alkali metal.

In certain embodiments, the present invention relates to compound I, wherein X is halide, acetate, or nitrate.

In certain embodiments, the present invention relates to compound I, wherein X is nitrate.

In certain embodiments, the present invention relates to compound I, wherein X is halide.

In certain embodiments, the present invention relates to compound I, wherein X is chloride or iodide.

In certain embodiments, the present invention relates to compound I, wherein $R^1$, $R^2$, and $R^3$ represent independently for each occurrence H; $R^4$ is methyl; and $R^5$ is fluorosubstituted aryl.

In certain embodiments, the present invention relates to compound I, wherein $R^1$, $R^2$, and $R^3$ represent independently for each occurrence H; $R^4$ is methyl; and $R^5$ is 4-fluorophenyl.

In certain embodiments, the present invention relates to compound I, wherein $R^1$, $R^2$, and $R^3$ represent independently for each occurrence H; $R^4$ is methyl; $R^5$ is 4-fluorophenyl; and X is chloride.

In certain embodiments, the present invention relates to compound I, wherein $R^1$ is phenyl, $R^2$ and $R^3$ represent independently for each occurrence H, $R^4$ is methyl, and $R^5$ is fluorosubstituted cycloalkyl.

In certain embodiments, the present invention relates to compound I, wherein $R^1$ is phenyl, $R^2$ and $R^3$ represent independently for each occurrence H, $R^4$ is methyl, and $R^5$ is 2-fluorocyclobutyl or 4-fluorocyclohexyl.

In certain embodiments, the present invention relates to compound I, wherein $R^1$ is phenyl, $R^2$ and $R^3$ represent independently for each occurrence H, $R^4$ is methyl, X is iodide, and $R^5$ is 2-fluorocyclobutyl or 4-fluorocyclohexyl.

In certain embodiments, the present invention relates to compound I, wherein the fluoro substituent of $R^5$ comprises $^{18}F$ at natural abundance.

Another aspect of the present invention relates to a compound represented by formula II:

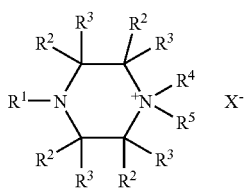

II wherein $R^1$ is fluorosubstituted alkyl, fluorosubstituted cycloalkyl, fluorosubstituted aryl, fluorosubstituted aralkyl, or fluorosubstituted alkenyl; wherein said fluoro substituent comprises $^{18}F$;

$R^2$ represents independently for each occurrence H, alkyl, halogen, hydroxyl, amino, aminoalkyl, or alkoxyl;

$R^3$ represents independently for each occurrence H, alkyl, or halogen;

$R^4$ is alkyl or aralkyl;

$R^5$ is H, alkyl, cycloalkyl, alkenyl, alkynyl, aryl, heteroaryl, aralkyl, heteroaralkyl, acyl, alkylsulfonyl, arylsulfonyl, aralkylsulfonyl, or —$CO_2R^6$;

X is an anion that has an overall charge of −1; and $R^6$ is H, alkyl, aryl, or aralkyl.

In certain embodiments, the present invention relates to compound II, wherein said compound has a radioactivity of greater than or equal to about 1 Curie/mmol.

In certain embodiments, the present invention relates to compound II, wherein said compound has a radioactivity of greater than or equal to about 5 Curie/mmol.

In certain embodiments, the present invention relates to compound II, wherein said compound has a radioactivity of greater than or equal to about 10 Curie/mmol.

In certain embodiments, the present invention relates to compound II, wherein said compound has a radioactivity of greater than or equal to about 100 Curie/mmol.

In certain embodiments, the present invention relates to compound II, wherein said compound has a radioactivity of greater than or equal to about 1,000 Curie/mmol.

In certain embodiments, the present invention relates to compound II, wherein $R^5$ is H, alkyl, cycloalkyl, or aryl.

In certain embodiments, the present invention relates to compound II, wherein $R^5$ is H.

In certain embodiments, the present invention relates to compound II, wherein $R^5$ is aryl.

In certain embodiments, the present invention relates to compound II, wherein $R^5$ is a phenyl group.

In certain embodiments, the present invention relates to compound II, wherein $R^2$ and $R^3$ represent independently for each occurrence H or alkyl.

In certain embodiments, the present invention relates to compound II, wherein $R^2$ and $R^3$ represent independently for each occurrence H.

In certain embodiments, the present invention relates to compound II, wherein $R^4$ is alkyl.

In certain embodiments, the present invention relates to compound II, wherein $R^4$ is methyl, ethyl, propyl, isopropyl, butyl, isobutyl, sec-butyl, or pentyl.

In certain embodiments, the present invention relates to compound II, wherein $R^4$ is methyl.

In certain embodiments, the present invention relates to compound II, wherein $R^1$ is fluorosubstituted alkyl, fluorosubstituted cycloalkyl, or fluorosubstituted aryl.

In certain embodiments, the present invention relates to compound II, wherein $R^1$ is fluorosubstituted cycloalkyl.

In certain embodiments, the present invention relates to compound II, wherein $R^1$ is fluorosubstituted cyclopropyl, fluorosubstituted cyclobutyl, fluorosubstituted cyclopentyl, fluorosubstituted cyclohexyl, fluorosubstituted cycloheptyl, or fluorosubstituted cyclooctyl.

In certain embodiments, the present invention relates to compound II, wherein $R^1$ is fluorosubstituted cyclobutyl or fluorosubstituted cyclohexyl.

In certain embodiments, the present invention relates to compound II, wherein $R^1$ is 2-fluorocyclobutyl or 4-fluorocyclohexyl.

In certain embodiments, the present invention relates to compound II, wherein $R^1$ is fluorosubstituted aryl.

In certain embodiments, the present invention relates to compound II, wherein $R^1$ is fluorosubstituted phenyl.

In certain embodiments, the present invention relates to compound II, wherein $R^1$ is 4-fluorophenyl.

In certain embodiments, the present invention relates to compound II, wherein X is halide, acetate, nitrate, sulfonate, $PO_4M_2$, $SO_4M$, valerate, oleate, palmitate, stearate, laurate, or benzoate; wherein M is alkali metal.

In certain embodiments, the present invention relates to compound II, wherein X is halide, acetate, or nitrate.

In certain embodiments, the present invention relates to compound II, wherein X is halide.

In certain embodiments, the present invention relates to compound II, wherein X is nitrate.

Another aspect of the present invention relates to a compound represented by formula III:

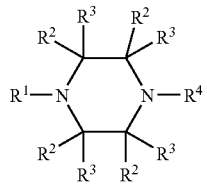

wherein $R^1$ is H, alkyl, cycloalkyl, alkenyl, alkynyl, aryl, heteroaryl, aralkyl, heteroaralkyl, acyl, alkylsulfonyl, arylsulfonyl, aralkylsulfonyl, or —$CO_2R^5$;

$R^2$ represents independently for each occurrence H, alkyl, halogen, hydroxyl, amino, aminoalkyl, or alkoxyl;

$R^3$ represents independently for each occurrence H, alkyl, or halogen;

$R^4$ is fluorosubstituted alkyl, fluorosubstituted cycloalkyl, fluorosubstituted aryl, fluorosubstituted aralkyl, or fluorosubstituted alkenyl; and said fluoro substituent comprises $^{18}F$;

X is an anion that has an overall charge of −1; and $R^5$ is H, alkyl, aryl, or aralkyl.

In certain embodiments, the present invention relates to compound III, wherein said compound has a radioactivity of greater than or equal to about 1 Curie/mmol.

In certain embodiments, the present invention relates to compound III, wherein said compound has a radioactivity of greater than or equal to about 5 Curie/mmol.

In certain embodiments, the present invention relates to compound III, wherein said compound has a radioactivity of greater than or equal to about 10 Curie/mmol.

In certain embodiments, the present invention relates to compound III, wherein said compound has a radioactivity of greater than or equal to about 100 Curie/mmol.

In certain embodiments, the present invention relates to compound III, wherein said compound has a radioactivity of greater than or equal to about 1,000 Curie/mmol.

In certain embodiments, the present invention relates to compound III, wherein $R^1$ is H, alkyl, cycloalkyl, or aryl.

In certain embodiments, the present invention relates to compound III, wherein $R^1$ is H.

In certain embodiments, the present invention relates to compound III, wherein $R^1$ is aryl.

In certain embodiments, the present invention relates to compound III, wherein $R^1$ is a phenyl group.

In certain embodiments, the present invention relates to compound III, wherein $R^2$ and $R^3$ represent independently for each occurrence H or alkyl.

In certain embodiments, the present invention relates to compound III, wherein $R^2$ and $R^3$ represent independently for each occurrence H.

In certain embodiments, the present invention relates to compound III, wherein $R^4$ is fluorosubstituted alkyl, fluorosubstituted cycloalkyl, or fluorosubstituted aryl.

In certain embodiments, the present invention relates to compound III, wherein $R^4$ is fluorosubstituted cycloalkyl.

In certain embodiments, the present invention relates to compound III, wherein $R^4$ is fluorosubstituted cyclopropyl, fluorosubstituted cyclobutyl, fluorosubstituted cyclopentyl, fluorosubstituted cyclohexyl, fluorosubstituted cycloheptyl, or fluorosubstituted cyclooctyl.

In certain embodiments, the present invention relates to compound III, wherein $R^4$ is fluorosubstituted cyclobutyl or fluorosubstituted cyclohexyl.

In certain embodiments, the present invention relates to compound III, wherein $R^4$ is 2-fluorocyclobutyl or 4-fluorocyclohexyl.

In certain embodiments, the present invention relates to compound III, wherein $R^4$ is fluorosubstituted aryl.

In certain embodiments, the present invention relates to compound III, wherein $R^4$ is fluorosubstituted phenyl.

In certain embodiments, the present invention relates to compound III, wherein $R^4$ is 4-fluorophenyl.

In certain embodiments, the present invention relates to compound III, wherein $R^1$, $R^2$, and $R^3$ represent independently for each occurrence H; and $R^4$ is fluorosubstituted aryl.

In certain embodiments, the present invention relates to compound III, wherein $R^1$, $R^2$, and $R^3$ represent independently for each occurrence H; and $R^4$ is 4-fluorophenyl.

In certain embodiments, the present invention relates to compound III, wherein $R^1$ is phenyl, $R^2$ and $R^3$ represent independently for each occurrence H, and $R^4$ is fluorosubstituted cycloalkyl.

In certain embodiments, the present invention relates to compound III, wherein $R^1$ is phenyl, $R^2$ and $R^3$ represent independently for each occurrence H, and $R^4$ is 2-fluorocyclobutyl or 4-fluorocyclohexyl.

In certain embodiments, the present invention relates to compound III, wherein the fluoro substituent of $R^5$ comprises $^{18}F$ at natural abundance.

Another aspect of the present invention relates to a compound represented by formula IV:

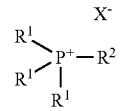

wherein $R^1$ represents independently for each occurrence aryl or heteroaryl;

$R^2$ is halogen-substituted alkyl, halogen-substituted cycloalkyl, halogen-substituted aryl, halogen-substituted aralkyl, halogen-substituted alkenyl; wherein said halogen substituent is flouride that comprises $^{18}F$, or said halogen substituent is iodide that comprises $^{123}I$, $^{124}I$, $^{125}I$, or $^{131}I$; and X is an anion that has an overall charge of −1.

In certain embodiments, the present invention relates to compound IV, wherein said halogen substituent of $R^2$ is fluoride that comprises $^{18}F$; and said compound has a radioactivity of greater than or equal to about 1 Curie/mmol.

In certain embodiments, the present invention relates to compound IV, wherein said halogen substituent of $R^2$ is fluoride that comprises $^{18}F$; and said compound has a radioactivity of greater than or equal to about 5 Curie/mmol.

In certain embodiments, the present invention relates to compound IV, wherein said halogen substituent of $R^2$ is fluoride that comprises $^{18}F$; and said compound has a radioactivity of greater than or equal to about 10 Curie/mmol.

In certain embodiments, the present invention relates to compound IV, wherein said halogen substituent of $R^2$ is fluoride that comprises 18F; and said compound has a radioactivity of greater than or equal to about 100 Curie/mmol.

In certain embodiments, the present invention relates to compound IV, wherein said halogen substituent of $R^2$ is fluoride that comprises $^{18}$F; and said compound has a radioactivity of greater than or equal to about 1,000 Curie/mmol.

In certain embodiments, the present invention relates to compound IV, wherein said halogen substituent of R$^2$ is iodide that comprises $^{123}$I; and said compound has a radioactivity of greater than or equal to about 1 Curie/mmol.

In certain embodiments, the present invention relates to compound IV, wherein said halogen substituent of R$^2$ is iodide that comprises $^{123}$I; and said compound has a radioactivity of greater than or equal to about 5 Curie/mmol.

In certain embodiments, the present invention relates to compound IV, wherein said halogen substituent of R$^2$ is iodide that comprises $^{123}$I; and said compound has a radioactivity of greater than or equal to about 10 Curie/mmol.

In certain embodiments, the present invention relates to compound IV, wherein said halogen substituent of R$^2$ is iodide that comprises $^{123}$I; and said compound has a radioactivity of greater than or equal to about 100 Curie/mmol.

In certain embodiments, the present invention relates to compound IV, wherein said halogen substituent of R$^2$ is iodide that comprises $^{123}$I; and said compound has a radioactivity of greater than or equal to about 1,000 Curie/mmol.

In certain embodiments, the present invention relates to compound IV, wherein said halogen substituent of R$^2$ is iodide that comprises $^{124}$I; and said compound has a radioactivity of greater than or equal to about 1 Curie/mmol.

In certain embodiments, the present invention relates to compound IV, wherein said halogen substituent of R$^2$ is iodide that comprises $^{124}$I; and said compound has a radioactivity of greater than or equal to about 5 Curie/mmol.

In certain embodiments, the present invention relates to compound IV, wherein said halogen substituent of R$^2$ is iodide that comprises $^{124}$I; and said compound has a radioactivity of greater than or equal to about 10 Curie/mmol.

In certain embodiments, the present invention relates to compound IV, wherein said halogen substituent of R$^2$ is iodide that comprises $^{124}$I; and said compound has a radioactivity of greater than or equal to about 100 Curie/mmol.

In certain embodiments, the present invention relates to compound IV, wherein said halogen substituent of R$^2$ is iodide that comprises $^{124}$I; and said compound has a radioactivity of greater than or equal to about 1,000 Curie/mmol.

In certain embodiments, the present invention relates to compound IV, wherein said halogen substituent of R$^2$ is iodide that comprises $^{125}$I; and said compound has a radioactivity of greater than or equal to about 1 Curie/mmol.

In certain embodiments, the present invention relates to compound IV, wherein said halogen substituent of R$^2$ is iodide that comprises $^{125}$I; and said compound has a radioactivity of greater than or equal to about 5 Curie/mmol.

In certain embodiments, the present invention relates to compound IV, wherein said halogen substituent of R$^2$ is iodide that comprises $^{125}$I; and said compound has a radioactivity of greater than or equal to about 10 Curie/mmol.

In certain embodiments, the present invention relates to compound IV, wherein said halogen substituent of R$^2$ is iodide that comprises $^{125}$I; and said compound has a radioactivity of greater than or equal to about 100 Curie/mmol.

In certain embodiments, the present invention relates to compound IV, wherein said halogen substituent of R$^2$ is iodide that comprises $^{125}$I; and said compound has a radioactivity of greater than or equal to about 1,000 Curie/mmol.

In certain embodiments, the present invention relates to compound IV, wherein said halogen substituent of R$^2$ is iodide that comprises $^{131}$I; and said compound has a radioactivity of greater than or equal to about 1 Curie/mmol.

In certain embodiments, the present invention relates to compound IV, wherein said halogen substituent of R$^2$ is iodide that comprises $^{131}$I; and said compound has a radioactivity of greater than or equal to about 5 Curie/mmol.

In certain embodiments, the present invention relates to compound IV, wherein said halogen substituent of R$^2$ is iodide that comprises $^{131}$I; and said compound has a radioactivity of greater than or equal to about 10 Curie/mmol.

In certain embodiments, the present invention relates to compound IV, wherein said halogen substituent of R$^2$ is iodide that comprises $^{131}$I; and said compound has a radioactivity of greater than or equal to about 100 Curie/mmol.

In certain embodiments, the present invention relates to compound IV, wherein said halogen substituent of R$^2$ is iodide that comprises $^{131}$I; and said compound has a radioactivity of greater than or equal to about 1,000 Curie/mmol.

In certain embodiments, the present invention relates to compound IV, wherein R$^1$ represents independently for each occurrence aryl.

In certain embodiments, the present invention relates to compound IV, wherein R$^1$ represents independently for each occurrence optionally substituted phenyl.

In certain embodiments, the present invention relates to compound IV, wherein R$^1$ represents independently for each occurrence phenyl.

In certain embodiments, the present invention relates to compound IV, wherein R$^2$ is halogen-substituted cycloalkyl or halogen-substituted aryl.

In certain embodiments, the present invention relates to compound IV, wherein R$^2$ is halogen-substituted aryl.

In certain embodiments, the present invention relates to compound IV, wherein R$^2$ is halogen-substituted phenyl.

In certain embodiments, the present invention relates to compound IV, wherein R$^1$ represents independently for each occurrence phenyl and R is 4-fluorophenyl.

In certain embodiments, the present invention relates to compound IV, wherein X is halide, acetate, nitrate, sulfonate, PO$_4$M$_2$, SO$_4$M, valerate, oleate, palmitate, stearate, laurate, or benzoate; wherein M is alkali metal.

In certain embodiments, the present invention relates to compound IV, wherein X is halide, acetate, or nitrate.

In certain embodiments, the present invention relates to compound IV, wherein X is nitrate.

In certain embodiments, the present invention relates to compound IV, wherein R$^1$ represents independently for each occurrence phenyl, R$^2$ is 4-fluorophenyl, and X is nitrate.

In certain embodiments, the present invention relates to compound IV, wherein R$^1$ represents independently for each occurrence phenyl, R$^2$ is 4-iodophenyl, and X is nitrate.

Another aspect of the present invention relates to a formulation, comprising a compound of formula I, II, III, or IV; and a pharmaceutically acceptable excipient.

Methods of the Invention

One aspect of the present invention relates to a method of making a halogenated compound as depicted in Scheme 1:

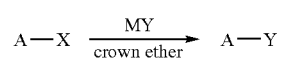

1 wherein

A is alkyl, cycloalkyl, aryl, heteroaryl, aralkyl, alkenyl or has the formula a or b:

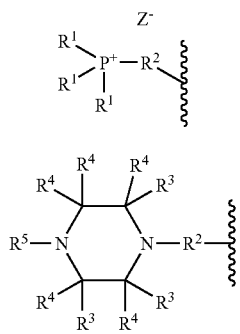

wherein
R$^1$ and R$^2$ represent independently for each occurrence alkyl, cycloalkyl, aryl, or heteroaryl;
R$^3$ represents independently for each occurrence H, alkyl, or halogen;
R$^4$ represents independently for each occurrence H, alkyl, halogen, hydroxyl, amino, aminoalkyl, or alkoxyl;
R$^5$ is H, alkyl, cycloalkyl, alkenyl, alkynyl, aryl, heteroaryl, aralkyl, heteroaralkyl, acyl, alkylsulfonyl, arylsulfonyl, aralkylsulfonyl, or —CO$_2$R$^5$; and
Z is halide, nitrate, acetate, benzoate, or sulfonate;
X is sulfonate, nitro, acetate, or halogen;
M is an alkali metal or transition metal;
Y is fluoride or iodide;
crown ether is a cyclic molecule in which oxygen atoms are connected by optionally substituted dimethylene linkages; and
the method is practiced under substantially anhydrous conditions.

In certain embodiments, the present invention relates to the aforementioned method, wherein Y is a radioactive fluoride or radioactive iodide.

In certain embodiments, the present invention relates to the aforementioned method, wherein Y is fluoride.

In certain embodiments, the present invention relates to the aforementioned method, wherein Y comprises $^{18}$F.

In certain embodiments, the present invention relates to the aforementioned method, wherein Y is fluoride that comprises $^{18}$F; and the radioactivity of MY, A-Y or both is greater than or equal to about 1 Curie/mmol.

In certain embodiments, the present invention relates to the aforementioned method, wherein Y is fluoride that comprises $^{18}$F; and the radioactivity of MY, A-Y or both is greater than or equal to about 5 Curie/mmol.

In certain embodiments, the present invention relates to the aforementioned method, wherein Y is fluoride that comprises $^{18}$F; and the radioactivity of MY, A-Y or both is greater than or equal to about 10 Curie/mmol.

In certain embodiments, the present invention relates to the aforementioned method, wherein Y is fluoride that comprises $^{18}$F; and the radioactivity of MY, A-Y or both is greater than or equal to about 100 Curie/mmol.

In certain embodiments, the present invention relates to the aforementioned method, wherein Y is fluoride that comprises $^{18}$F; and the radioactivity of MY, A-Y or both is greater than or equal to about 1,000 Curie/mmol.

In certain embodiments, the present invention relates to the aforementioned method, wherein Y comprises $^{123}$I.

In certain embodiments, the present invention relates to the aforementioned method, wherein Y is iodide that comprises $^{123}$I; and the radioactivity of MY, A-Y or both is greater than or equal to about 1 Curie/mmol.

In certain embodiments, the present invention relates to the aforementioned method, wherein Y is iodide that comprises $^{123}$I; and the radioactivity of MY, A-Y or both is greater than or equal to about 5 Curie/mmol.

In certain embodiments, the present invention relates to the aforementioned method, wherein Y is iodide that comprises $^{123}$I; and the radioactivity of MY, A-Y or both is greater than or equal to about 10 Curie/mmol.

In certain embodiments, the present invention relates to the aforementioned method, wherein Y is iodide that comprises $^{123}$I; and the radioactivity of MY, A-Y or both is greater than or equal to about 100 Curie/mmol.

In certain embodiments, the present invention relates to the aforementioned method, wherein Y is iodide that comprises $^{123}$I; and the radioactivity of MY, A-Y or both is greater than or equal to about 1,000 Curie/mmol.

In certain embodiments, the present invention relates to the aforementioned method, wherein Y comprises $^{124}$I.

In certain embodiments, the present invention relates to the aforementioned method, wherein Y is iodide that comprises $^{124}$I; and the radioactivity of MY, A-Y or both is greater than or equal to about 1 Curie/mmol.

In certain embodiments, the present invention relates to the aforementioned method, wherein Y is iodide that comprises $^{124}$I; and the radioactivity of MY, A-Y or both is greater than or equal to about 5 Curie/mmol.

In certain embodiments, the present invention relates to the aforementioned method, wherein Y is iodide that comprises $^{124}$I; and the radioactivity of MY, A-Y or both is greater than or equal to about 10 Curie/mmol.

In certain embodiments, the present invention relates to the aforementioned method, wherein Y is iodide that comprises $^{124}$I; and the radioactivity of MY, A-Y or both is greater than or equal to about 100 Curie/mmol.

In certain embodiments, the present invention relates to the aforementioned method, wherein Y is iodide that comprises $^{124}$I; and the radioactivity of MY, A-Y or both is greater than or equal to about 1,000 Curie/mmol.

In certain embodiments, the present invention relates to the aforementioned method, wherein Y comprises $^{125}$I.

In certain embodiments, the present invention relates to the aforementioned method, wherein Y is iodide that comprises $^{125}$I; and the radioactivity of MY, A-Y or both is greater than or equal to about 1 Curie/mmol.

In certain embodiments, the present invention relates to the aforementioned method, wherein Y is iodide that comprises $^{125}$I; and the radioactivity of MY, A-Y or both is greater than or equal to about 5 Curie/mmol.

In certain embodiments, the present invention relates to the aforementioned method, wherein Y is iodide that comprises $^{125}$I; and the radioactivity of MY, A-Y or both is greater than or equal to about 10 Curie/mmol.

In certain embodiments, the present invention relates to the aforementioned method, wherein Y is iodide that comprises $^{125}$I; and the radioactivity of MY, A-Y or both is greater than or equal to about 100 Curie/mmol.

In certain embodiments, the present invention relates to the aforementioned method, wherein Y is iodide that comprises $^{125}$I; and the radioactivity of MY, A-Y or both is greater than or equal to about 1,000 Curie/mmol.

In certain embodiments, the present invention relates to the aforementioned method, wherein Y comprises $^{131}$I.

In certain embodiments, the present invention relates to the aforementioned method, wherein Y is iodide that comprises $^{131}$I; and the radioactivity of MY, A-Y or both is greater than or equal to about 1 Curie/mmol.

In certain embodiments, the present invention relates to the aforementioned method, wherein Y is iodide that comprises $^{131}$I; and the radioactivity of MY, A-Y or both is greater than or equal to about 5 Curie/mmol.

In certain embodiments, the present invention relates to the aforementioned method, wherein Y is iodide that comprises $^{131}$I; and the radioactivity of MY, A-Y or both is greater than or equal to about 10 Curie/mmol.

In certain embodiments, the present invention relates to the aforementioned method, wherein Y is iodide that comprises $^{131}$I; and the radioactivity of MY, A-Y or both is greater than or equal to about 100 Curie/mmol.

In certain embodiments, the present invention relates to the aforementioned method, wherein Y is iodide that comprises $^{131}$I; and the radioactivity of MY, A-Y or both is greater than or equal to about 1,000 Curie/mmol.

In certain embodiments, the present invention relates to the aforementioned method, wherein the method is practiced under anhydrous conditions.

In certain embodiments, the present invention relates to the aforementioned method, wherein A is alkyl, cycloalkyl, or aryl.

In certain embodiments, the present invention relates to the aforementioned method, wherein A is alkyl.

In certain embodiments, the present invention relates to the aforementioned method, wherein A is alkyl and said alkyl group is substituted by X at a primary carbon atom.

In certain embodiments, the present invention relates to the aforementioned method, wherein A is alkyl and said alkyl group is substituted by X at a secondary carbon atom.

In certain embodiments, the present invention relates to the aforementioned method, wherein A is cycloalkyl.

In certain embodiments, the present invention relates to the aforementioned method, wherein A is cycloalkyl and said alkyl group is substituted by X at a secondary carbon atom.

In certain embodiments, the present invention relates to the aforementioned method, wherein A is cyclopropyl, cyclobutyl, cyclopentyl, cyclohexyl, cycloheptyl, or cyclooctyl.

In certain embodiments, the present invention relates to the aforementioned method, wherein A is cyclobutyl or cyclohexyl.

In certain embodiments, the present invention relates to the aforementioned method, wherein A has the formula a:

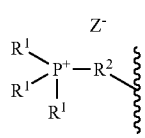

a wherein
  $R^1$ and $R^2$ represent independently for each occurrence alkyl, cycloalkyl, aryl, or heteroaryl; and
  Z is halide, nitrate, acetate, benzoate, or sulfonate.

In certain embodiments, the present invention relates to the aforementioned method, wherein A has the formula b:

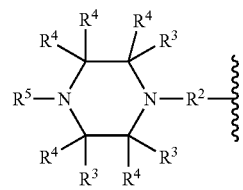

b wherein
  $R^2$ represents independently for each occurrence alkyl, cycloalkyl, aryl, or heteroaryl;
  $R^3$ represents independently for each occurrence H, alkyl, or halogen;
  $R^4$ represents independently for each occurrence H, alkyl, halogen, hydroxyl, amino, aminoalkyl, or alkoxyl; and
  $R^5$ is H, alkyl, cycloalkyl, alkenyl, alkynyl, aryl, heteroaryl, aralkyl, heteroaralkyl, acyl, alkylsulfonyl, arylsulfonyl, aralkylsulfonyl, or —$CO_2R^5$.

In certain embodiments, the present invention relates to the aforementioned method, wherein A has the formula a:

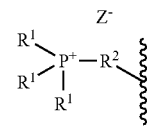

a wherein
  $R^1$ and $R^2$ represent independently for each occurrence aryl; and
  Z is nitrate.

In certain embodiments, the present invention relates to the aforementioned method, wherein A has the formula a:

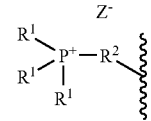

a wherein
  $R^1$ and $R^2$ represent independently for each occurrence optionally substituted phenyl; and
  Z is nitrate.

In certain embodiments, the present invention relates to the aforementioned method, wherein A has the formula b:

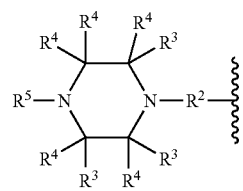

b wherein
  $R^2$ represents cycloalkyl;

R³ represents H;
R⁴ represents H; and
R⁵ is H or aryl.

In certain embodiments, the present invention relates to the aforementioned method, wherein X is sulfonate or nitro.

In certain embodiments, the present invention relates to the aforementioned method, wherein X is methanesulfonate or trifluoromethanesulfonate.

In certain embodiments, the present invention relates to the aforementioned method, wherein M is an alkali metal.

In certain embodiments, the present invention relates to the aforementioned method, wherein M is potassium, sodium, or lithium.

In certain embodiments, the present invention relates to the aforementioned method, wherein M is potassium.

In certain embodiments, the present invention relates to the aforementioned method, wherein said crown ether is Kryptofix.

In certain embodiments, the present invention relates to the aforementioned method, wherein said crown ether is selected from the group consisting of 1,4,10-Trioxa-7,13-diaza-cyclopentadecane (Kryptofix® 21), 4,7,13,16,21,24-Hexaoxa-1,10-diazabicyclo[8.8.8] hexacosane (Kryptofix® 222), 4,7,13,16,21-Pentaoxa-1,10-diazabicyclo[8.8.5]tricosane (Kryptofix® 221), and 4,7,13,18-Tetraoxa-1,10-diazabicyclo[8.5.5]eicosane (Kryptofix® 211).

In certain embodiments, the present invention relates to the aforementioned method, wherein the reaction temperature is between about 50° C. and about 220° C.

In certain embodiments, the present invention relates to the aforementioned method, wherein the reaction temperature is between about 100° C. and about 200° C.

In certain embodiments, the present invention relates to the aforementioned method, wherein the reaction is conducted in the presence of solvent.

In certain embodiments, the present invention relates to the aforementioned method, wherein the reaction is conducted in the presence of acetonitrile.

In certain embodiments, the present invention relates to the aforementioned method, wherein said MY is anhydrous.

In certain embodiments, the present invention relates to the aforementioned method, wherein said MY contains less than about 2% water.

In certain embodiments, the present invention relates to the aforementioned method, wherein said MY contains less than about 1% water.

In certain embodiments, the present invention relates to the aforementioned method, wherein said MY contains less than about 0.5% water.

In certain embodiments, the present invention relates to the aforementioned method, wherein A is alkyl, X is sulfonate, M is potassium, Y comprises ¹⁸F, and said crown either is Kryptofix.

In certain embodiments, the present invention relates to the aforementioned method, wherein A is alkyl, X is methanesulfonate, M is potassium, Y comprises ¹⁸F, and said crown either is Kryptofix.

In certain embodiments, the present invention relates to the aforementioned method, wherein A is cycloalkyl, X is sulfonate, M is potassium, Y comprises ¹⁸F, and said crown either is Kryptofix.

In certain embodiments, the present invention relates to the aforementioned method, wherein A is cycloalkyl, X is methanesulfonate, M is potassium, Y comprises ¹⁸F, and said crown either is Kryptofix.

In certain embodiments, the present invention relates to the aforementioned method, wherein X is methanesulfonate, M is potassium, Y comprises ¹⁸F, crown either is Kryptofix, and A is optionally subsituted cyclobutyl or optionally subsituted cyclohexyl.

In certain embodiments, the present invention relates to the aforementioned method, wherein X is methanesulfonate, M is potassium, Y comprises ¹⁸F, crown either is Kryptofix, and A is cyclobutyl or cyclohexyl.

In certain embodiments, the present invention relates to the aforementioned method, wherein A is aryl, X is nitro, M is potassium, Y comprises ¹⁸F, and said crown either is Kryptofix.

In certain embodiments, the present invention relates to the aforementioned method, wherein A is optionally substituted phenyl, X is nitro, M is potassium, Y comprises ¹⁸F, and said crown either is Kryptofix.

In certain embodiments, the present invention relates to the aforementioned method, wherein A is cycloalkyl, X is methanesulfonate, M is potassium, Y comprises ¹⁸F, crown either is Kryptofix, and the reaction temperature is between about 100° C. and about 200° C.

In certain embodiments, the present invention relates to the aforementioned method, wherein A is aryl, X is nitro, M is potassium, Y comprises ¹⁸F, and said crown either is Kryptofix, and the reaction temperature is between about 100° C. and about 200° C.

In certain embodiments, the present invention relates to the aforementioned method, wherein X is nitro, M is potassium, Y comprises ¹⁸F, and said crown either is Kryptofix, and the reaction temperature is between about 100° C. and about 200° C., and A has the formula a:

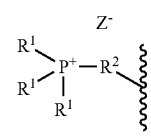

wherein
R¹ and R² represent independently for each occurrence optionally substituted phenyl; and
Z is nitrate.

In certain embodiments, the present invention relates to the aforementioned method, wherein X is methanesulfonate or trifluoromethanesulfonate; M is potassium; said crown ether is Kryptofix; Y comprises ¹⁸F; and A has the formula b:

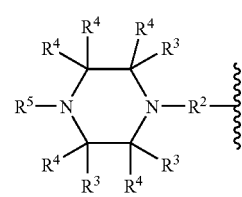

wherein
R² represents cycloalkyl;
R³ represents independently for each occurrence H;
R⁴ represents independently for each occurrence H; and
R⁵ is H or aryl.

Another aspect of the present invention relates to a method of making a halogenated compound as depicted in Scheme 2:

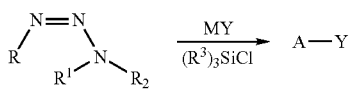

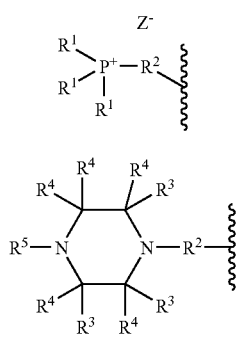

wherein
- $R^1$ and $R^2$ represent indepently for each occurrence alkyl, aryl, aralkyl, or $R^1$ and $R^2$ taken together form a cycloalkyl group;
- R is alkenyl, aryl, heteroaryl, or has the formula a or b:

wherein
- $R^1$ and $R^2$ represent independently for each occurrence alkyl, cycloalkyl, aryl, or heteroaryl;
- $R^3$ represents independently for each occurrence H, alkyl, or halogen;
- $R^4$ represents independently for each occurrence H, alkyl, halogen, hydroxyl, amino, aminoalkyl, or alkoxyl;
- $R^5$ is H, alkyl, cycloalkyl, alkenyl, alkynyl, aryl, heteroaryl, aralkyl, heteroaralkyl, acyl, alkylsulfonyl, arylsulfonyl, aralkylsulfonyl, or $-CO_2R^5$; and
- Z is halide, nitrate, acetate, benzoate, or sulfonate;
- M is an alkali metal, transition metal, or tetralkylammonium salt;
- Y is fluoride or iodide; and
- $R^3$ represents independently for each occurrence alkyl, aryl, or aralkyl.

In certain embodiments, the present invention relates to the aforementioned method, wherein Y is fluoride.

In certain embodiments, the present invention relates to the aforementioned method, wherein Y is iodide.

In certain embodiments, the present invention relates to the aforementioned method, wherein Y comprises $^{18}F$.

In certain embodiments, the present invention relates to the aforementioned method, wherein Y is fluoride that comprises 18F; and the radioactivity of MY, A-Y or both is greater than or equal to about 1 Curie/mmol.

In certain embodiments, the present invention relates to the aforementioned method, wherein Y is fluoride that comprises $^{18}F$; and the radioactivity of MY, A-Y or both is greater than or equal to about 5 Curie/mmol.

In certain embodiments, the present invention relates to the aforementioned method, wherein Y is fluoride that comprises $^{18}F$; and the radioactivity of MY, A-Y or both is greater than or equal to about 10 Curie/mmol.

In certain embodiments, the present invention relates to the aforementioned method, wherein Y is fluoride that comprises $^{18}F$; and the radioactivity of MY, A-Y or both is greater than or equal to about 100 Curie/mmol.

In certain embodiments, the present invention relates to the aforementioned method, wherein Y is fluoride that comprises $^{18}F$; and the radioactivity of MY, A-Y or both is greater than or equal to about 1,000 Curie/mmol.

In certain embodiments, the present invention relates to the aforementioned method, wherein Y comprises $^{123}I$.

In certain embodiments, the present invention relates to the aforementioned method, wherein Y is iodide that comprises $^{123}I$; and the radioactivity of MY, A-Y or both is greater than or equal to about 1 Curie/mmol.

In certain embodiments, the present invention relates to the aforementioned method, wherein Y is iodide that comprises $^{123}I$; and the radioactivity of MY, A-Y or both is greater than or equal to about 5 Curie/mmol.

In certain embodiments, the present invention relates to the aforementioned method, wherein Y is iodide that comprises $^{123}I$; and the radioactivity of MY, A-Y or both is greater than or equal to about 10 Curie/mmol.

In certain embodiments, the present invention relates to the aforementioned method, wherein Y is iodide that comprises $^{123}I$; and the radioactivity of MY, A-Y or both is greater than or equal to about 100 Curie/mmol.

In certain embodiments, the present invention relates to the aforementioned method, wherein Y is iodide that comprises $^{123}I$; and the radioactivity of MY, A-Y or both is greater than or equal to about 1,000 Curie/mmol.

In certain embodiments, the present invention relates to the aforementioned method, wherein Y comprises $^{124}I$.

In certain embodiments, the present invention relates to the aforementioned method, wherein Y is iodide that comprises $^{124}I$; and the radioactivity of MY, A-Y or both is greater than or equal to about 1 Curie/mmol.

In certain embodiments, the present invention relates to the aforementioned method, wherein Y is iodide that comprises $^{124}I$; and the radioactivity of MY, A-Y or both is greater than or equal to about 5 Curie/mmol.

In certain embodiments, the present invention relates to the aforementioned method, wherein Y is iodide that comprises $^{124}I$; and the radioactivity of MY, A-Y or both is greater than or equal to about 10 Curie/mmol.

In certain embodiments, the present invention relates to the aforementioned method, wherein Y is iodide that comprises $^{124}I$; and the radioactivity of MY, A-Y or both is greater than or equal to about 100 Curie/mmol.

In certain embodiments, the present invention relates to the aforementioned method, wherein Y is iodide that comprises $^{124}I$; and the radioactivity of MY, A-Y or both is greater than or equal to about 1,000 Curie/mmol.

In certain embodiments, the present invention relates to the aforementioned method, wherein Y comprises $^{125}I$.

In certain embodiments, the present invention relates to the aforementioned method, wherein Y is iodide that comprises $^{125}I$; and the radioactivity of MY, A-Y or both is greater than or equal to about 1 Curie/mmol.

In certain embodiments, the present invention relates to the aforementioned method, wherein Y is iodide that comprises $^{125}I$; and the radioactivity of MY, A-Y or both is greater than or equal to about 5 Curie/mmol.

In certain embodiments, the present invention relates to the aforementioned method, wherein Y is iodide that comprises $^{125}I$; and the radioactivity of MY, A-Y or both is greater than or equal to about 10 Curie/mmol.

In certain embodiments, the present invention relates to the aforementioned method, wherein Y is iodide that comprises $^{125}$I; and the radioactivity of MY, A-Y or both is greater than or equal to about 100 Curie/mmol.

In certain embodiments, the present invention relates to the aforementioned method, wherein Y is iodide that comprises $^{125}$I; and the radioactivity of MY, A-Y or both is greater than or equal to about 1,000 Curie/mmol.

In certain embodiments, the present invention relates to the aforementioned method, wherein Y comprises $^{131}$I.

In certain embodiments, the present invention relates to the aforementioned method, wherein Y is iodide that comprises $^{131}$I; and the radioactivity of MY, A-Y or both is greater than or equal to about 1 Curie/mmol.

In certain embodiments, the present invention relates to the aforementioned method, wherein Y is iodide that comprises $^{131}$I; and the radioactivity of MY, A-Y or both is greater than or equal to about 5 Curie/mmol.

In certain embodiments, the present invention relates to the aforementioned method, wherein Y is iodide that comprises $^{131}$I; and the radioactivity of MY, A-Y or both is greater than or equal to about 10 Curie/mmol.

In certain embodiments, the present invention relates to the aforementioned method, wherein Y is iodide that comprises $^{131}$I; and the radioactivity of MY, A-Y or both is greater than or equal to about 100 Curie/mmol.

In certain embodiments, the present invention relates to the aforementioned method, wherein Y is iodide that comprises $^{131}$I; and the radioactivity of MY, A-Y or both is greater than or equal to about 1,000 Curie/mmol.

In certain embodiments, the present invention relates to the aforementioned method, wherein the method is practiced under anhydrous conditions.

In certain embodiments, the present invention relates to the aforementioned method, wherein R is aryl.

In certain embodiments, the present invention relates to the aforementioned method, wherein R has the formula a:

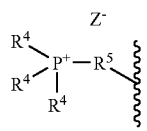

wherein
  $R^4$ and $R^5$ represent independently for each occurrence alkyl, cycloalkyl, aryl, or heteroaryl; and
  Z is halide, nitrate, acetate, benzoate, or sulfonate.

In certain embodiments, the present invention relates to the aforementioned method, wherein R has the formula a:

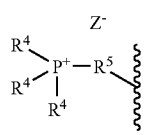

wherein
  $R^4$ and $R^5$ represent independently for each occurrence aryl; and
  Z is halide.

In certain embodiments, the present invention relates to the aforementioned method, wherein $R^1$ and $R^2$ are taken together to form a cycloalkyl group.

In certain embodiments, the present invention relates to the aforementioned method, wherein M is an alkali metal.

In certain embodiments, the present invention relates to the aforementioned method, wherein M is potassium, sodium, or lithium.

In certain embodiments, the present invention relates to the aforementioned method, wherein M is sodium.

In certain embodiments, the present invention relates to the aforementioned method, wherein $R^3$ represents independently for each occurrence alkyl.

In certain embodiments, the present invention relates to the aforementioned method, wherein $R^3$ represents independently for each occurrence methyl, ethyl, propyl, isopropyl, or butyl.

In certain embodiments, the present invention relates to the aforementioned method, wherein $R^3$ represents independently for each occurrence methyl.

In certain embodiments, the present invention relates to the aforementioned method, wherein M is sodium, Y comprises Iodide-125, $R^3$ represents independently for each occurrence methyl, $R^1$ and $R^2$ are taken together to form a cycloalkyl group, and R has the formula a:

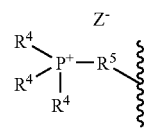

wherein
  $R^4$ and $R^5$ represent independently for each occurrence aryl; and
  Z is halide.

In certain embodiments, the present invention relates to the aforementioned method, wherein M is sodium, Y comprises Iodide-125, $R^3$ represents independently for each occurrence methyl, $R^1$ and $R^2$ are taken together to form a cyclohexyl group, and R has the formula a:

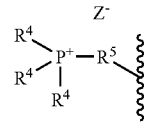

wherein
  $R^4$ and $R^5$ represent independently for each occurrence optionally substituted phenyl; and
  Z is iodide.

Another aspect of the present invention relates to a method of obtaining a positron emission image of a portion of a mammal, comprising the steps of:
  administering to a mammal a compound of formula I, II, III, or IV and acquiring a positron emission spectrum of a portion of said mammal.

In certain embodiments, the present invention relates to the aforementioned method, wherein said compound is represented by formula I.

In certain embodiments, the present invention relates to the aforementioned method, wherein said compound is represented by formula II.

In certain embodiments, the present invention relates to the aforementioned method, wherein said compound is represented by formula III.

In certain embodiments, the present invention relates to the aforementioned method, wherein said compound is represented by formula IV.

In certain embodiments, the present invention relates to the aforementioned method, wherein said mammal is a human, mouse, rat, dog, feline, monkey, guinea pig, or rabbit.

In certain embodiments, the present invention relates to the aforementioned method, wherein said mammal is a human.

Another aspect of the present invention relates to a method of measuring blood flow in the heart of a mammal, comprising the steps of:

administering to a mammal a compound of formula I, II, III, or IV and acquiring a positron emission spectrum of a portion of said mammal.

In certain embodiments, the present invention relates to the aforementioned method, wherein said compound is represented by formula I.

In certain embodiments, the present invention relates to the aforementioned method, wherein said compound is represented by formula II.

In certain embodiments, the present invention relates to the aforementioned method, wherein said compound is represented by formula III.

In certain embodiments, the present invention relates to the aforementioned method, wherein said compound is represented by formula IV.

In certain embodiments, the present invention relates to the aforementioned method, wherein said mammal is a human, mouse, rat, dog, feline, monkey, guinea pig, or rabbit.

In certain embodiments, the present invention relates to the aforementioned method, wherein said mammal is a human.

Another aspect of the present invention relates to a method of measuring membrane transport in a mammal, comprising the steps of:

administering to a mammal a compound of formula I, II, III, or IV and acquiring a positron emission spectrum of a portion of said mammal.

In certain embodiments, the present invention relates to the aforementioned method, wherein said compound is represented by formula I.

In certain embodiments, the present invention relates to the aforementioned method, wherein said compound is represented by formula II.

In certain embodiments, the present invention relates to the aforementioned method, wherein said compound is represented by formula III.

In certain embodiments, the present invention relates to the aforementioned method, wherein said compound is represented by formula IV.

In certain embodiments, the present invention relates to the aforementioned method, wherein said mammal is a human, mouse, rat, dog, feline, monkey, guinea pig, or rabbit.

In certain embodiments, the present invention relates to the aforementioned method, wherein said mammal is a human.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective a mount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha., .beta. or gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention maybe prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween.RTM. and Pluronic.RTM. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Combinatorial Libraries

The subject compounds may be synthesized using the methods of combinatorial synthesis described in this section. Combinatorial libraries of the compounds may be used for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131-5135; and U.S. Pat. Nos. 4,631,211; 5,440, 016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging With Sequenceable Bio-Oligomers

The principle of using oligonucleotides to encode combinatorial synthetic libraries was described in 1992 (Brenner et al. (1992) *PNAS* 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar a nomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

EXAMPLE 1

Synthesis of [F-18]-1-methyl-1-(4-fluorophenyl)piperazinium Salt

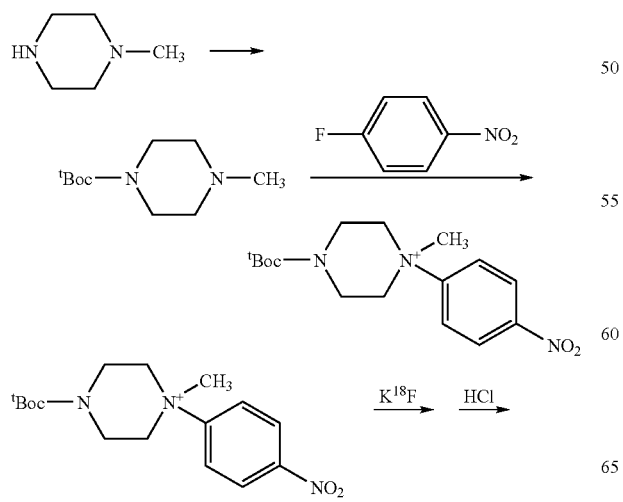

-continued

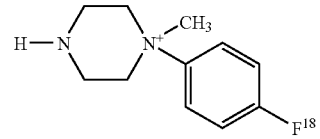

t-BOC-Protected methylpiperizine was heated in the presence of 1-fluoro-4-nitrobenzene under pressure in benzene to give 4-t-BOC-protected 1-methyl-1-(4-nitrophenyl)piperazinium salt. The piperazinium salt was heated in the presence of potassium [$^{18}$F]fluoride and Krytofix at 200° C. for 10 minutes. The oil was treated with aq. 3 M HCl for 20 minutes to give [F-18]-1-methyl-1-(4-fluorophenyl)piperazinium chloride.

EXAMPLE 2

Synthesis of [F-18]-1-(4-fluorocyclohexyl)-1-methyl-4-phenylpiperazinium Iodide

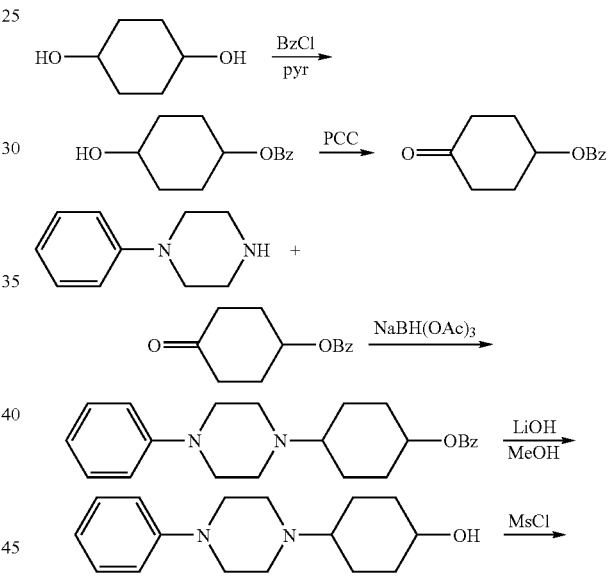

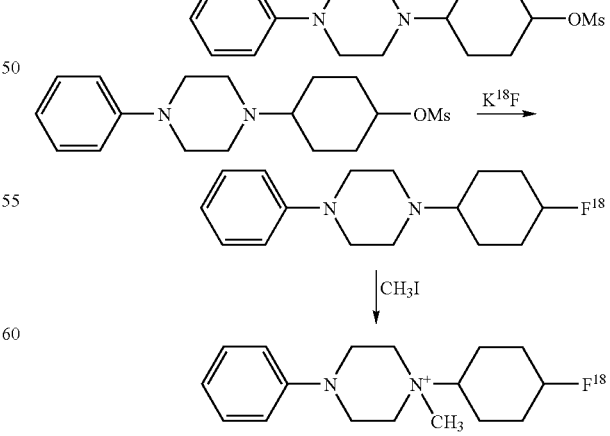

A solution of 1,4-cyclohexadiol (cis/trans mixture, 10 g, 86 mmol), benzoyl chloride (12 g, 86 mmol), and DMAP (50 mg) in methylene chloride/pyridine (80/20) was stirred at 25° C. for 4 hr. The reaction mixture washed with 10% HCl until the aqueous layer was acidic and methylene chloride layer was washed with sat'd NaHCO$_3$, brine, and dried (Na$_2$SO$_4$). After solvent removal, chromatography (silica gel, methylene chloride/methanol, 95:5) of the crude material gave 6 g (30%) of the benzoyl alcohol.

4-Benzoylcyclohexanol (5 g, 23 mmol) was oxidized using PCC (7.4 g, 34.5) mmol) in methylene chloride (50 mL) for 2 hours at 25° C. The black reaction mixture was filtered through a short bed of silica gel and solvent was removed. Chromatography (silica gel, hexane/ethyl acetate, 85:15) afforded 3 g (60%) of the ketone; Mp 58-60° C.

Reductive amination to give 1-(4-benzoyoxycyclohexyl)-4-phenylpiperazine was done using a published procedure [*J. Org. Chem.* 1996, 61, 3849-3862]. 1-Phenylpiperazine (1 g, 6.2 mmol) and 4-benzoyoxycyclohexanone (1.4 g, 6.2 mmol) were mixed in 1,2-dichoroethane (35 mL) and then treated with sodium triacetoxyborohydride (1.2 g) and glacial acetic acid (0.25 g). The mixture was stirred at 25° C. under nitrogen for 16 hours. The reaction mixture was quenched by adding 1 N NaOH (20 mL) and the product was extracted with methylene chloride. The extract was washed with brine, dried (MgSO$_4$), and solvent was evaporated to give the crude free base. Chromatography (silica gel, methylene chloride, 95:5) afforded 1.8 g (80%) of 1-(4-benzoyoxycyclohexyl)-4-phenylpiperazine.

Deprotection of 1-(4-benzoyoxycyclohexyl)-4-phenylpiperazine (1 g, 2.7 mmol) was done in methanol (25 mL) using 1M lithium hydroxide (5 mL) at 80° C. for 1 hr, which gave 0.6 g (85%) of 1-(4-hydroxycyclohexyl)-4-phenylpiperazine.

1-(4-Hydroxycyclohexyl)-4-phenylpiperazine (0.5 g, 1.9 mmol) was converted to the mesylate using methane sulfonyl chloride (0.23 g, 2 mmol) in 10 mL of methylene chloride/pyridine (90/10) at 25° C. The reaction mixture was stirred for 2 hours and volatiles were removed under vacuum. The crude product was dissolved in methylene chloride (20 mL) and washed with sat'd NaHCO$_3$ twice and dried (MgSO$_4$). After solvent removal, the crude product was chromatographed on silica gel using methylene chloride/methanol (90:10), which gave 0.4 g (80%) of the piperazine mesylate. $^1$H NMR (CDCl$_3$), δ1.4-2.4 (9H, m, ring-CH), 2.7 (4H, m, piperazine-CH$_2$), 3.05 (3H, s, CH$_3$), 3.2 (4H, m, piperazine-CH$_2$), 4.6 (1H, m, O—CH), 6.83-6.9 (2H, m, phenyl-CH), 7.2-7.3 (3H, m, phenyl-CH).

A Wheaton 5-mL reaction vial containing fluorine-18 (20 mCi) in 0.5 mL of $^{18}$O-enriched water, Kryptofix 2.2.2 (10 mg), and potassium carbonate (2 mg) was heated at 118° C. and solvent was evaporated with the aid of a nitrogen gas flow. The K$^{18}$F/Kryptofix complex was dried three times by the addition of 1 mL of acetonitrile followed by evaporation of the solvent using a nitrogen flow. A solution of 5 mg of 1-(4-methanesulfonyoxycyclohexyl)-4-phenylpiperazine in 1 ml of acetonitrile was added to the vial and the fluorination reaction was performed at 120° C. for 10 min. Solvent was removed using a nitrogen flow and replaced with 1 mL of a hexane/ethyl acetate/methanol (50:45:5) solution. After mixing, the solution was loaded onto a silica gel SepPak (Waters, Milford, Mass.) and the activity was eluted with 2 mL of the same solution. The labeled piperazine derivative was purified by HPLC (semi-prep silica gel column, hexane/ethyl acetate/methanol, 50:45:5). The solvent was removed and iodomethane (0.1 mL) in acetonitrile (1 mL) was added to a vial containing the activity. The reaction vial was heat at 120° C. for 20 minutes and solvent was evaporated to afford [F-18]-1-(4-fluorophenyl)-1-methylpiperazinium iodide (7 mCi).

EXAMPLE 3

Synthesis of [F-18]-1-(3-fluorocyclobutyl)-1-methyl-4-phenylpiperazinium iodide

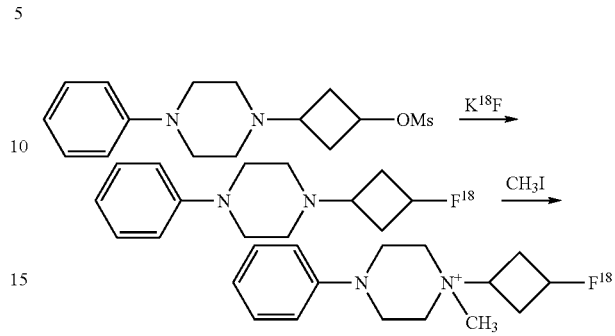

Cyclobutanone-4-benzyloxy ether was prepared by a published procedure [J. Am. Chem. Soc. 1971, 93, 130; Bull. Chem. Soc. Jpn, 1988, 57, 1637]. Reductive amination to give 1-(3-benzoxycyclobutyl)-4-phenylpiperazine was done using the published procedure [J. Org. Chem. 1996, 61, 3849-3862] use for the cyclohexyl analog. Hydrogenation, formation of the mesylate, and radio-labeling was done as described above.

EXAMPLE 4

Synthesis of [F-18]-(4-fluorophenyl)triphenylphosphonium Nitrate (FTTP)

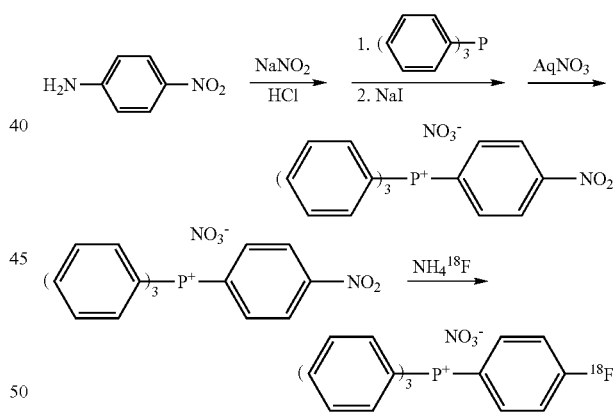

Non-radioactive standards and compounds used for radiolabeling were prepared by the method of Homer [*Chem. Ber.* 1958, 91, 45] and Rieke [*J. Am. Chem. Soc.* 1976, 98, 6872]. 4-Nitroaniline (2.8 g, 0.02 mol) and the molar equivalent of sodium nitrite were dissolved in 10 ml of concentrated HCl acid 10 ml of water at 0° C. Water (20 ml), in which was dissolved sodium acetate (5.6 g), was added. Triphenylphosphine (5.6 g) dissolved in ethyl acetate (80 ml) was added dropwise with stirring. After one hour, the resulting solution was acidified, the water layer separated from the ethyl acetate, and the aqueous portion extracted twice with ether. The ethyl acetate solution was extracted twice with water, the extracts were combined with the other aqueous fraction. Addition of an aqueous solution of sodium iodide precipitated the phosphonium iodide, mp 225-227° C. (Lit. 228.5° C.; *Chem. Ber.*

1958, 91, 45). 4-Nitrophenylphosphonium iodide was dissolved in 5 mL of ethanol treated with an aqueous solution of $AgNO_3$. The silver iodide was removed by filtration and the solution was evaporated to dryness. Chromatography of the crude salt on silica gel (methylene chloride/methanol (90: 10)) afforded pure 4-nitrophenylphosphonium nitrate; mp 215-127° C. Anal. calcd for $C_{24}H_{19}N_2O_5P$: C, 64.57; H, 4.29; Found: C, 64.49; H, 4.14.

[$^{18}$F]FTPP was prepared from 4-nitrophenyltriphenylphosphonium nitrate and [$^{18}$F]fluoride by nucleophilic aromatic substitution. A Wheaton 5-mL reaction vial containing fluorine-18 (600 mCi) in 1 mL of $^{18}$O-enriched water and 100 μL of ammonia hydroxide was heated at 120° C. and water was evaporated to near dryness (about 25 μL) with the aid of a nitrogen gas stream. A 1 mL solution of the nitro compound in acetonitrile was added to the vial and water and solvent were removed by evaporation. The contents were dried three times by the addition of 1 mL of acetonitrile followed by evaporation of solvent using a nitrogen flow. The reaction vial was heated at 200° C. for 10 min, cooled to 25° C., and the contents were dissolved in 1 ml of a 50% 0.1M $Ca(NO_3)_2$ in acetonitrile. The solution was loaded onto a alumunia SepPak (Waters, Milford, Mass.) to remove unreacted fluoride and the product purified by HPLC (Waters: Bondapak C-18, 19×150 mm column, flow: 6 mL/min; eluent: 50:50 acetonitrile/aqueous 0.01M $H_3PO_4$). Solvent was removed by roto-evaporation and [$^{18}$F]FTPP was dissolved in saline, the pH adjusted to 7.0 using sodium bicarbonate, and filtered (0.22 μm, Millipore:Millex-GV). Synthesis was completed within two hours; yield of [$^{18}$F]FTPP was 20 mCi (6% EOB).

EXAMPLE 5

Synthesis of [F-18]-(4-fluoro-3-nitrophenyl)triphenylphosphonium Nitrate

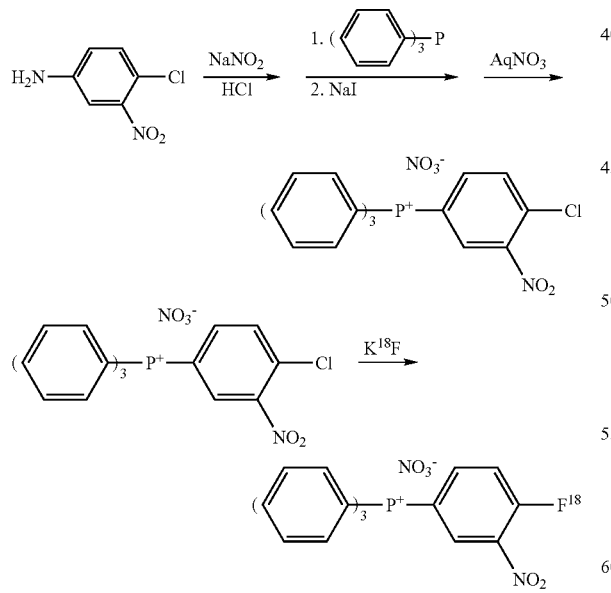

The meta nitro analog was prepared in the same manner as that described for [F-18]-(4-fluorophenyl)triphenyl-phosphonium nitrate.

[$^{18}$F]FTPP was prepared from (4-nitrophenyl)triphenylphosphonium nitrate and [$^{18}$F]fluoride by nucleophilic aromatic substitution. A Wheaton 5-mL reaction vial containing fluorine-18 (600 mCi) in 0.5 mL of $^{18}$O-enriched water and 100 μL of ammonia hydroxide was heated at 120° C. and water was evaporated to near dryness (~25 μL) with the aid of a nitrogen gas stream. A 1 mL solution of the nitro compound in acetonitrile was added to the vial and water and solvent were removed by evaporation. The contents were dried three times by the addition of 1 mL of acetonitrile followed by evaporation of solvent using a nitrogen flow. The reaction vial was heated at 200° C. for 10 min, cooled to 25° C., and the contents were dissolved in 0.5 ml of acetonitrile. The solution was loaded onto a silica SepPak (Waters, Milford, Mass.) to remove unreacted fluoride and the crude product was eluted with 10% methanol in methylene chloride (4 mL). After removal of the solvent by evaporation, the residue was dissolved in 50/50 acetonitrile:aqueous 0.01M $H_3PO_4$ and purified by HPLC (Waters:Bondapak C-18 19×150 mm column, flow:6 mL/min; eluent:same solvent). Solvent was removed by roto-evaporation and [$^{18}$F]FTPP was dissolved in saline, the pH adjusted to 7.5 using sodium bicarbonate, and filtered (0.22 μm, Millipore:Millex-GV). Synthesis was completed within two hrs; yield of [$^{18}$F]FTPP was 10 mCi (3% EOB).

EXAMPLE 6

Synthesis of [I-125]-p-iodophenyltriphenylphosponium Nitrate (ITPP)

Synthesis of I-125 labeled 4-iodophenyltriphenylphosphonium (ITPP) regiospecifically from the triazene, 4-piperidinylazophenyltriphenylphosphonium iodide, was reported by Shoup and Elmaleh. Triazenes have been well utilized for the preparation of high specific activity receptor probes and this route offers high yields and purity. Conversion of 4-iodoaniline to the triazene was done by trapping the diazonium ion with piperazine. The triazene was treated with triphenylphosphine and a catalytic amount of palladium (II) acetate to give the final precursor for I-125 labeling.

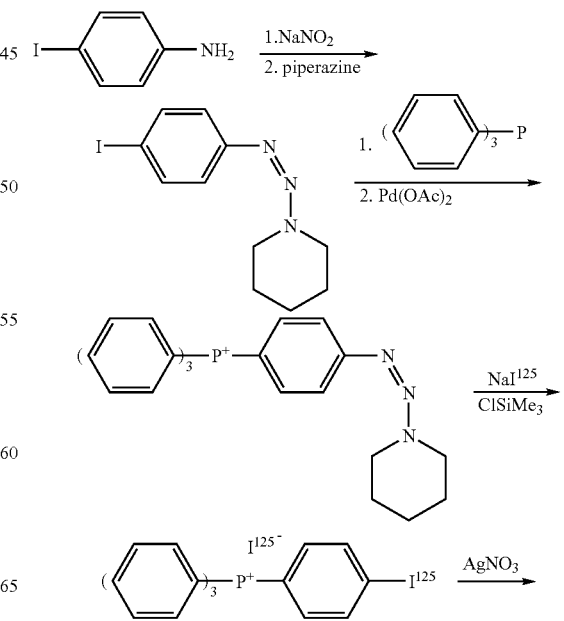

-continued

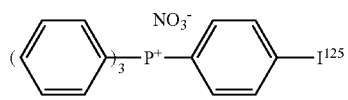

A mixture of 5.5 g (25.1 mmol) of 4-iodoaniline in 48 mL 6N-HCl was cooled in the ice-salt bath. To the mixture was added a precooled solution of 1.89 g (27.4 mmol) of $NaNO_2$ in 12 mL $H_2O$. After stirring for 10 min., an ice cold solution of 5.81 mL (58.7 mmol) of piperidine in 10.5 g of KOH in 90 mL $H_2O$ was added and stirring was continued. After 10 min., ammonia was added until it became basic and the product was extracted into $CH_2Cl_2$:EtOAc (1:1). The crude compound was purified by silica gel column chromatography by 30% methylene chloride in hexane elution to give 2.1 g (25.4%). An analytical sample was recrystallized from hexane: mp 63-65° C. NMR: d 1.70 (s, 6H), 3.78 (s, 4H), 7.19 and 7.63 (d, J=8.7 Hz, 4H). Anal. Calcd for $C_{11}H_{14}IN_3$: C, 41.92; H, 4.48; N, 13.33; I, 40.27. Found: C, 42.08; H, 4.60; N, 12.99; I, 4.075.

Palladium (II) acetate (4.48 mg, 0.02 mmol) was added to a solution of 630 mg (2 mmol) of triazene and 524 mg (2 mmol) of triphenylphosphine in xylene and the mixture was stirred at 110° C. overnight. The precipitate was filtered off and washed with benzene, and dried to give 167 mg (14.5%) as a solid which was used without further purification. An analytical sample was prepared by further purification on silica gel column by eluting with methylene chloride and recrystallization from $CH_2Cl_2$-Ether: mp 255-257° C. NMR: d 1.75 (m, 6H), 3.96 (m, 4H), 7.72 (m, 19H). Anal. calcd for $C_{29}H_{29}IN_3P$: C, 60.32; H, 5.06; N, 7.28; I, 21.98; P, 5.36. Found: C, 59.70; H, 5.14; N, 7.33; I, 21.65; P, 5.30.

Sodium$^{125}$I (340 µCi) was dried in a Reaction vial under azeotropic conditions with MeCN at 110° C. under a stream of nitrogen. 600 µg of triazene from the previous reaction, 30 µL of MeCN, and 5 µL of $ClSiMe_3$ were added to the vial and the mixture was heated at 60° C.

After 15 min. 100 µL of $NaHCO_3$ solution was added and the reaction mixture was extracted with $CH_2Cl_2$. The organic phase was washed three times thoroughly with 20% $AgNO_3$ solution. After evaporating the solvent, the crude product was dissolved in 0.1 mL $CH_2Cl_2$ and passed through a silica gel plug. This mini column was eluted with $CH_2Cl_2$ and acetone, respectively. The acetone fraction gave the desired product which was homogeneous on Radio-TLC (10% MeOH in $CH_2Cl_2$). The radiochemical yield was 67% and the specific activity was 17.4 Ci/mg.

EXAMPLE 7

Cell and Biodistribution of [I-125]-p-iodophenyltriphenylphosponium Nitrate (TPPI)

Figure 2:
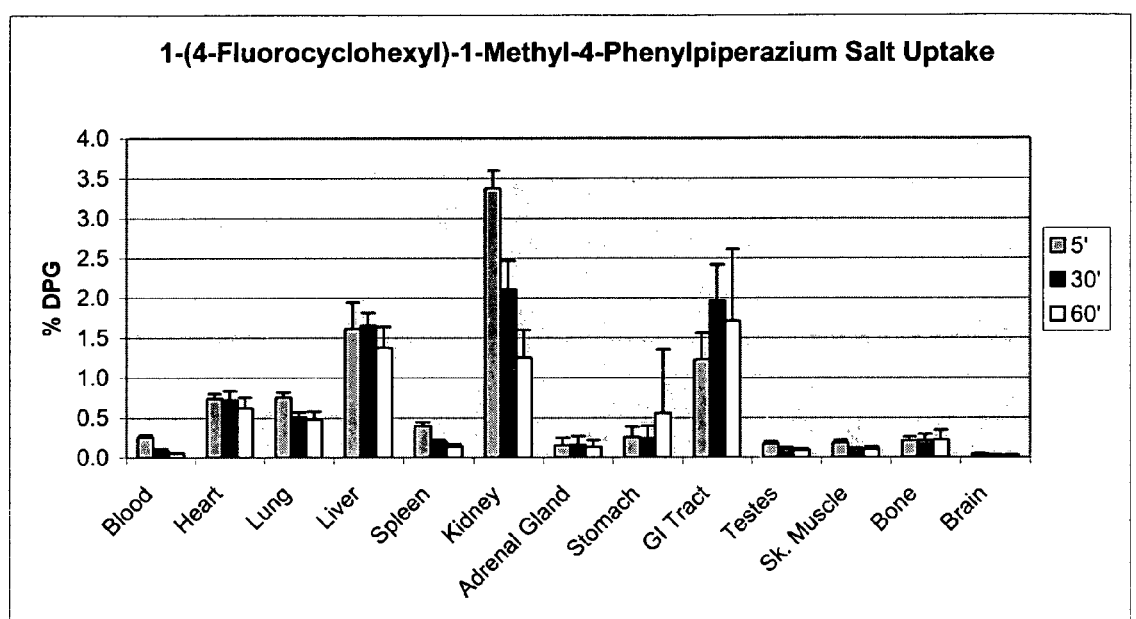
FIG. 2 depicts biodistribution data in rats for [F-18]1-(4-Fluorocyclohexyl)-1-Methyl-4-Phenylpiperazium.

The biodistribution of TPPI in rats (6 per time point) at 5, 30, and 60 minutes is presented in FIG. 2. Heart activity was over 0.7% dose per gram. The activity remained constant in the heart for a period of 60 min as expected from a microsphere. The activity washed fast from blood and heart-to-blood ratio increased from 2.9, 8.3 to 12.1 respectively. Heart-to-lung ratio changed from 0.96, 1.62 to 1.5. The heart density is twice that of the lung allowing for clear imaging of the heart especially in tomographic imaging.

Figure 3:
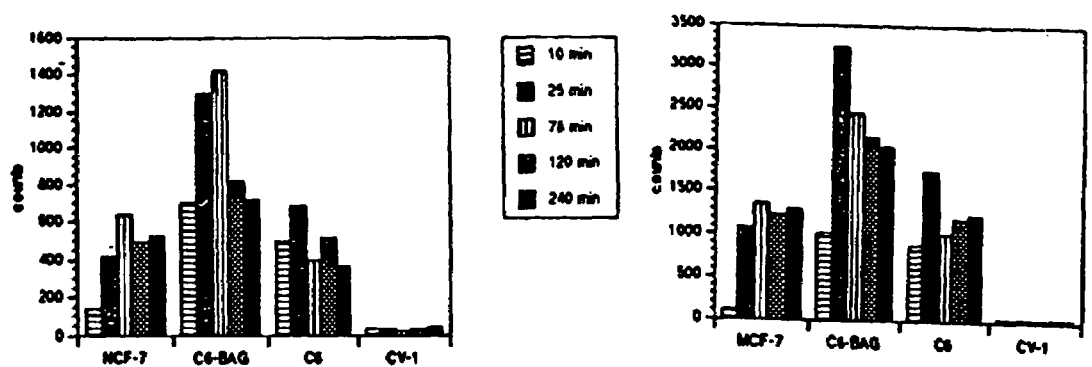
FIG. 3 depicts cell distribution data of [I-125]TPPI (Example 7).

The cell distribution of TPPI mimics that of its tritiated analog; the compound was accumulated and retained by carcinoma cells. High retention was observed in M CF-7 and C-6BAG glioma for a period of 240 minutes. The C6 glioma cell line showed partial washout from the maximum accumulation at 30 minutes. The CV-1 normal cell line stayed constant with no significant uptake. FIG. 3 indicates that both tritiated tetraphenylphosphonium and its radioiodinated version TPPI behave in the same manner.

Figure 4:
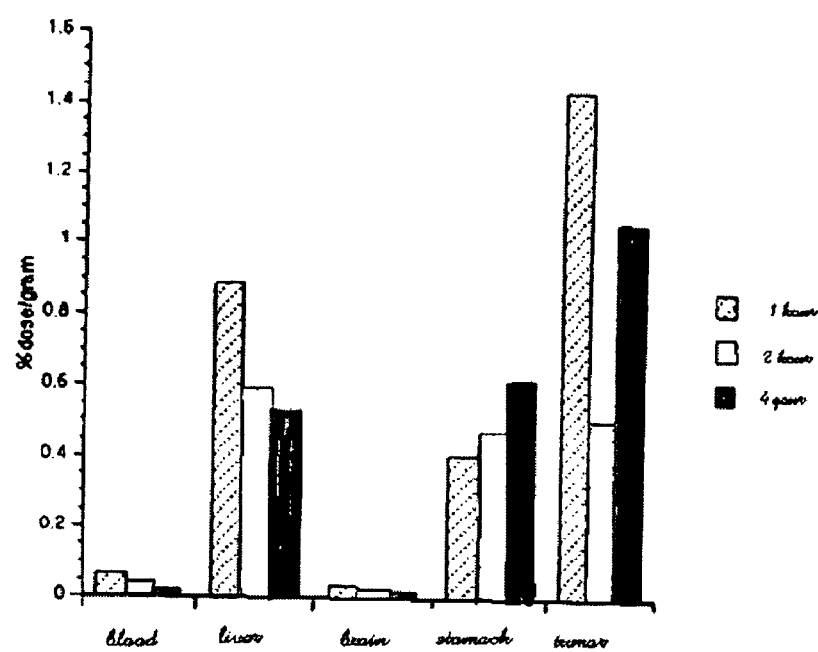
FIG. 4 depicts biodistribution of [I-125]TPPI in rats implanted with C6-BAG glioma (Example 7).

The biodistribution of TPPI in rats implanted with C6-BAG glioma shows that the radio-iodinated accumulated in the tumor tissue. The tumor-to-brain ratio at 60, 120, and 240 minutes was 40, 17 and 44, respectively. Tumor-to-blood ratios were 12 at all times. The lower-brain-to-tumor ratio measured at 120 minutes was due to the small average tumor size of this group. In general, brain uptake could be associated in part with breakdown of the blood-brain barrier. Since there was no washout from the tumor at 240 minutes, it is reasonable to assume that the high observed retention is at least in part due to the selective uptake mechanism of TPPI. FIG. 4 summarizes the biodistribution of TPPI in rats implanted with C6-BAG glioma in brain. Uptake is expressed in % dose/gram.

EXAMPLE 8

Cell and Biodistribution of [F-18]-(4-fluorophenyl)triphenylphosphonium Nitrate (FTTP)

FTTP in saline (50-75 µCi) was injected directly into the femoral vein of each non-anesthetized rat and the animals were sacrificed and evaluated at five time points: 5, 30, and 60 min (six rats per time point). Blood was obtained by cardiac puncture. Syringes will be weighed before and after injection to determine the volume delivered. Thqe activity per unit volume was obtained from standards. A total of eight different tissues (blood, bone, lung, liver, kidneys, heart, muscle, and whole brain) were excised, weighed and counted with a Packard Cobra II Auto-Gamma Counter (Packard Instrument Co., Downers Grove, Ill.). The raw counts were decay-corrected. All results are expressed as the percentage injected dose per gram (% ID/g; mean ±SD)

Figure 5:
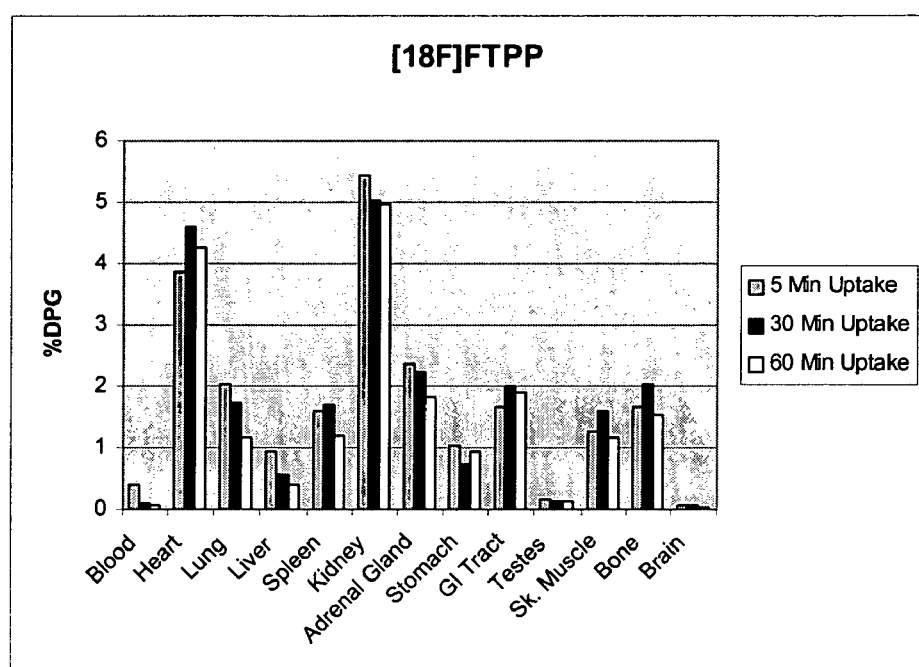
FIG. 5 depicts biodistribution in rats for [F-18](4-fluorophenyl)triphenylphosphonium (TPPF).
Figure 6:
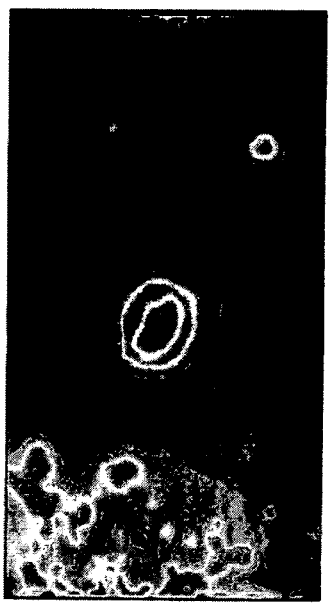
FIG. 6 depicts images of rat-heart slices (coronal (left), transverse (center), suggital (right)) obtained with a Micro-PET camera after injection of [F-18](4-fluorophenyl)triphenyl-phosphonium salt {[F-18]FTPP}.
Figure 6:
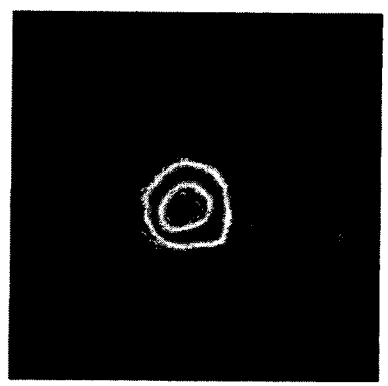
Figure 6:
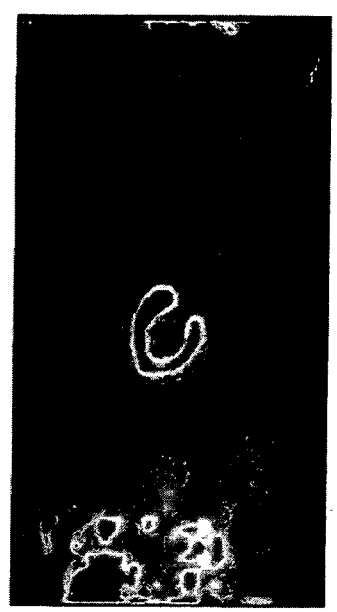
Figure 7:
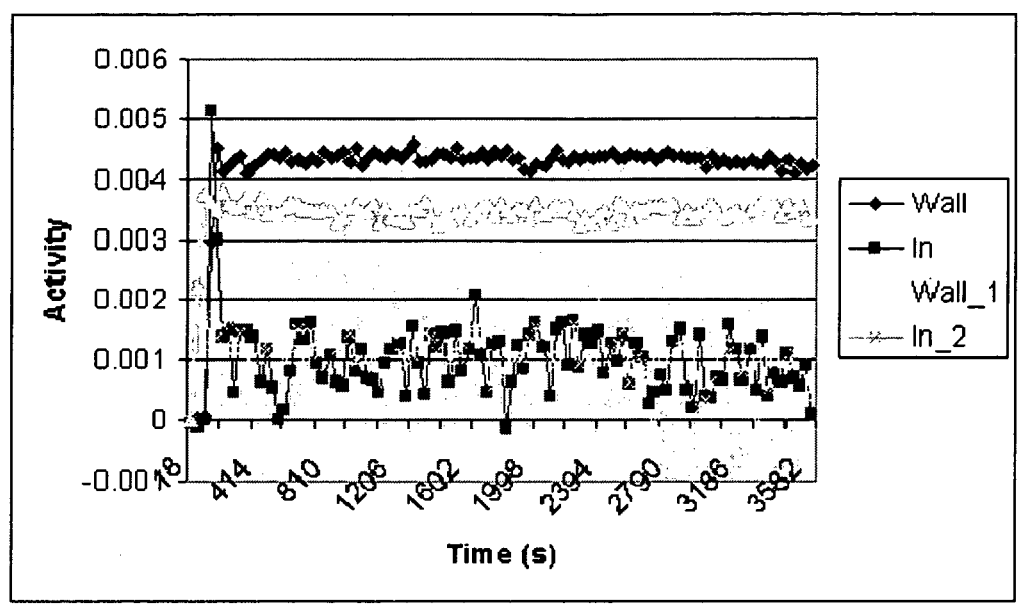
FIG. 7 depicts a time activity curve of rat heart obtained after IV injection of [F-18](4-fluorophenyl)triphenyl-phosphonium nitrate (normal state yellow) and after second injection of [F-18](4-fluorophenyl)triphenyl-phosphonium nitrate and an adenosine bolus injection (blue). A 29% increase in flow was observed.
Figure 8:
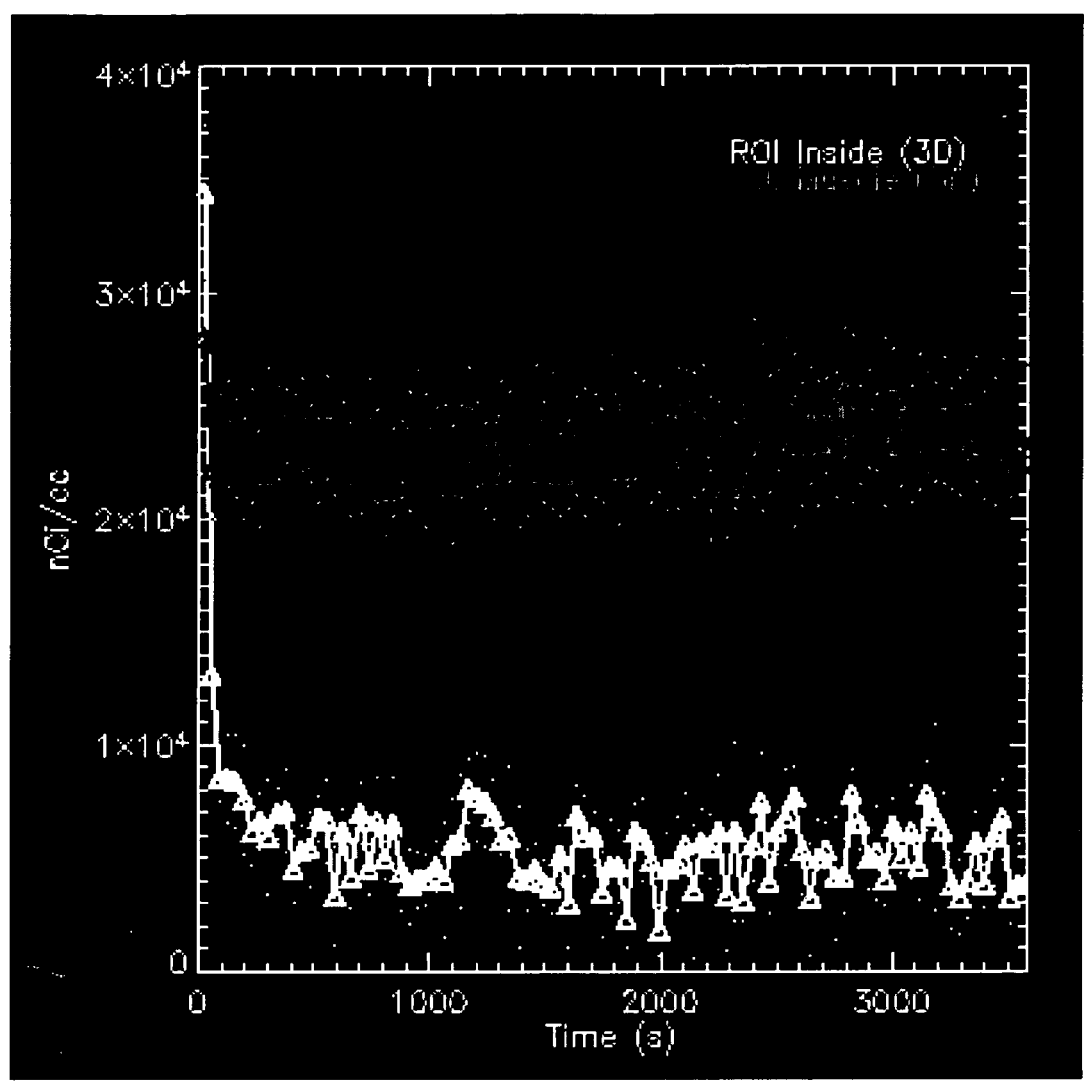
FIG. 8 depicts time-dependent activity of FTTP in blood pool inside the left ventricle (bottom) and in heart mussle (top).
Figure 9:
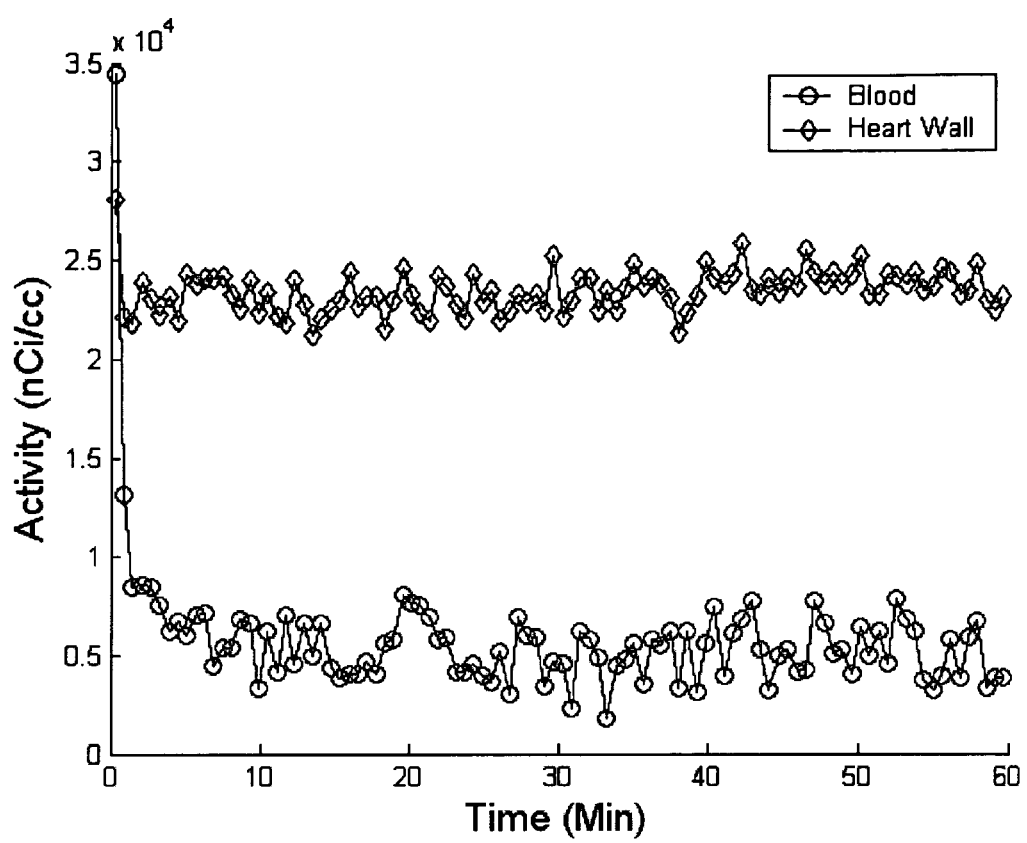
FIG. 9 depicts time-dependent activity of FTTP in blood pool inside the left ventricle and in heart mussle.

FIG. 5 shows the biodistribution of FTPP at 5, 30 and 60 min after intravenous administration in rats (5 per time point). At 5 min, accumulation of FTPP in the heart (1.64 ID/g) was 11-fold higher than in blood and 5-fold higher than in liver. Accumulation of FTPP in lungs, liver, and kidneys was greater than in blood, muscle, and brain. At 30 min, uptake of radioactivity in the heart was 1.5 ID/g and the heart-to-blood ratio was 75:1 (Table 1). Blood activity changed significantly from 5 to 60 min. Lung activity was 0.69 ID/g at 5 min, 0.30 ID/g at 30 min, 0.38 ID/g at 60 min, while liver uptake was 0.18 ID/g at 5 min, 0.17 ID/g at 30 min, 0.17 ID/g at 60 min. Heart-to-lung ratios at 5, 30 and 60 min were 2.4, 5.0, 3.2 and, respectively. Bone accumulation, an indication of defluorination, was minimal; 0.31 ID/g at 5 min and increased to 0.39 ID/g after 60 min.

TABLE 1

Heart-to-tissue ratios for FTTP at 5, 30, and 60 min post administration

| | Ratios (% ID/g) | | |
|---|---|---|---|
| | 5 min | 30 min | 60 min |
| Heart/Blood | 11 | 75 | 70 |
| Heart/Lung | 2 | 5 | 4 |
| Heart/Liver | 5 | 8 | 8 |

EXAMPLE 9

PET Imaging with [F-18]-(4-fluorophenyl)triphenylphosphonium Nitrate (FTTP)

Rats (250-300 grams) or rabbits (3-4 Kg) were anesthetized and placed ventrally to the imaging position and 0.4-1 mCi of the FTPP was injected into the vain. Three-dimensional dynamic data were acquired in list mode for one hour starting from the injection of the radiolabeled ligand.

PET imaging was conducted with a microPET, P4 system (Concorde Microsystems Inc, Knoxville, Tenn.). The length of the field of view is 8 cm and the diameter is 22 cm allowing entire upper body imaging of the rat or rabbit during a single acquisition. The imaging parameters of this system are in-plane and axial resolution of 1.2 mm full width of photopeak measured at half maximal count. MicroPET imaging of both animal species showed heart uptake after injection of FTPP with an initial spike of activity corresponding to blood flow followed by a plateau after 1 min. FIG. 2 is a representative images of midlevel axial (left), coronal (middle), sagital (left) views collected at 30-31 min post FTPP administration and typical blood and tissue time-activity curves obtained from sequential imaging for a period of one hour in a rat.

Figure 10:
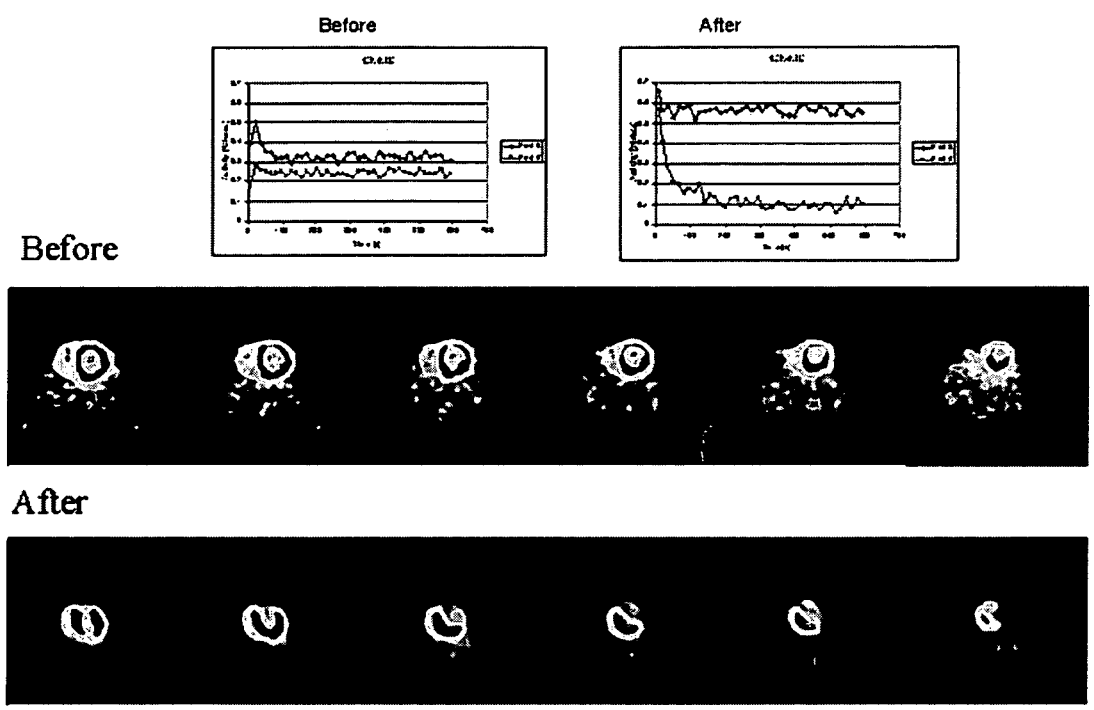
FIG. 10 depicts N-13-ammonia images and time activity curves before and after LAD occlusion.
Figure 11:
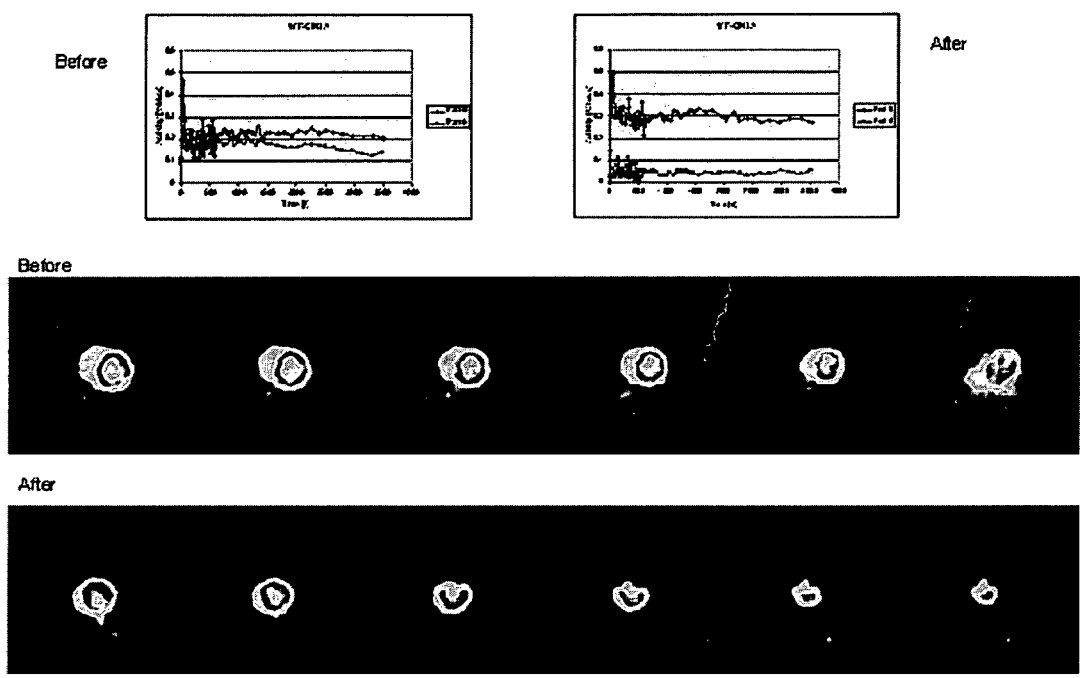
FIG. 11 depicts FTTP tomogramps and time activity curves of a rabbit before and after LAD occulusion.
Figure 12:
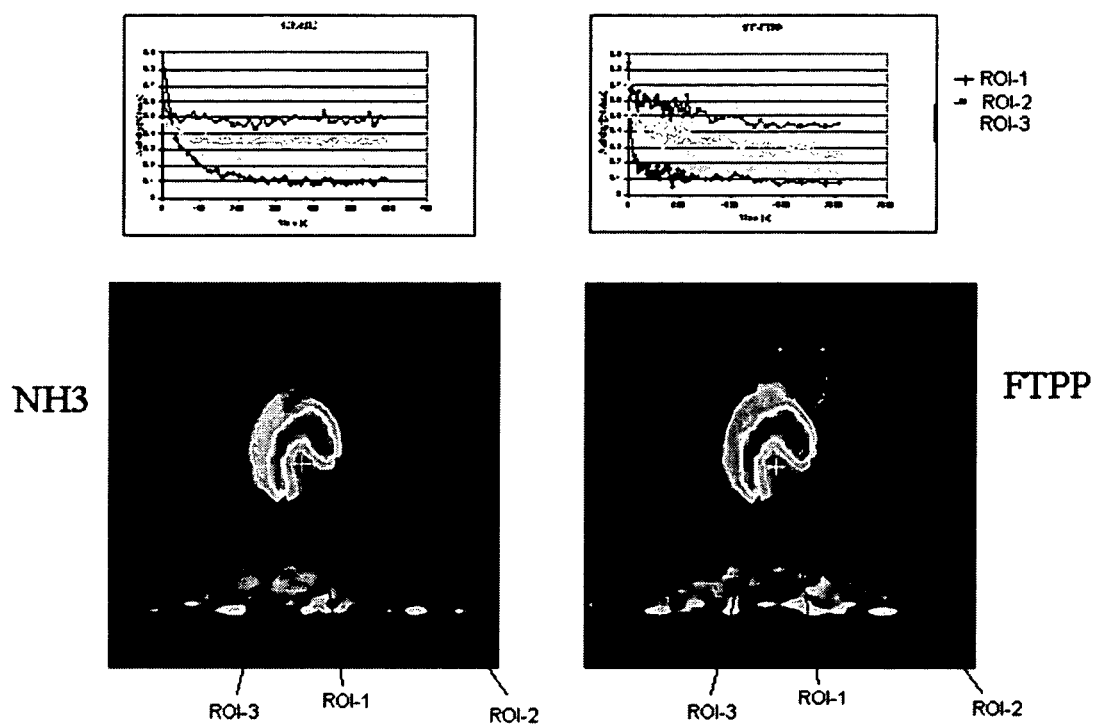
FIG. 12 depicts N-13-ammonia and FTTP images and their corresponding time activity curves post LAD occlusion (ROI analysis).

FIGS. 10 and 11 are several heart tomographs obtained from a rabbit before and after LAD occlusion performed on the next day in the same animal. The rabbit was anesthetized, placed in the microPET camera (body marks in the camera positioning were made) and sequential images were obtained for ten minutes following the administration of 3 mCi of N-13-ammonia (FIG. 10). One hour later, FTPP was injected followed by 60 minute sequential imaging of the rabbit (FIG. 11). Image corrections for the remaining N-13-ammonia activity were made with an appropriate program. One day later, the same rabbit underwent an LAD occlusion protocol, positioned in the same camera field of view and the above dual agent imaging sequence was repeated. FIGS. 10 and 11 represent several heart levels and time-activity curves of the normal rabbit on the first day injected with N-13-ammonia and FTTP, respectively. FIGS. 12 and 13 are the imaging results obtained after LAD occlusion in one section affected by occlusion. The time-activity curves and images clearly indicate the area of diminished activity in the LAD occlusion. The high quality rabbit images show similar clearer delineation of the heart muscle with FTTP compared to N-13-ammonia, an established myocardial perfusion agent. Late images at 60 min exhibited high myocardial retention of FTTP.

INCORPORATION BY REFERENCE

All of the U.S. patents and U.S. patent application publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula IV:

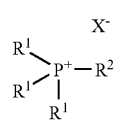

wherein
$R^1$ represents phenyl;
$R^2$ is $F^{18}$-4-fluorophenyl; and
X is an anion that has an overall charge of −1.

2. The compound of claim 1, wherein said compound has a radioactivity of greater than or equal to about 1 Curie/mmol.

3. The compound of claim 1, wherein compound has a radioactivity of greater than or equal to about 100 Curie/mmol.

4. The compound of claim 1, wherein X is halide, acetate, or nitrate.

5. The compound of claim 1, wherein X is nitrate.

6. A formulation, comprising a compound of claim 1; and a pharmaceutically acceptable excipient.

* * * * *

UNITED STATES PATENT AND TRADEMARK OFFICE
CERTIFICATE OF CORRECTION

PATENT NO. : 7,632,485 B2  Page 1 of 1
APPLICATION NO. : 11/065345
DATED : December 15, 2009
INVENTOR(S) : Elmaleh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this

Second Day of November, 2010

David J. Kappos
*Director of the United States Patent and Trademark Office*